United States Patent
Fleischman et al.

(10) Patent No.: US 6,830,576 B2
(45) Date of Patent: *Dec. 14, 2004

(54) APPARATUS FOR ELECTRICALLY ISOLATING A PORTION OF THE ATRIA

(75) Inventors: Sidney D. Fleischman, Menlo Park, CA (US); James G. Whayne, Saratoga, CA (US); Thomas M. Bourne, Mountain View, CA (US); David K. Swanson, Mountain View, CA (US)

(73) Assignee: EP Technologies, Inc., San Jose, CA (US)

( * ) Notice: Subject to any disclaimer, the term of this patent is extended or adjusted under 35 U.S.C. 154(b) by 176 days.

This patent is subject to a terminal disclaimer.

(21) Appl. No.: 10/098,695

(22) Filed: Mar. 15, 2002

(65) Prior Publication Data

US 2002/0111636 A1 Aug. 15, 2002

Related U.S. Application Data

(63) Continuation of application No. 09/524,263, filed on Mar. 13, 2000, now Pat. No. 6,379,366, which is a continuation of application No. 08/483,991, filed on Jun. 7, 1995, now Pat. No. 6,132,438.

(51) Int. Cl.[7] ............................................. A61B 17/04
(52) U.S. Cl. ..................................................... 606/139
(58) Field of Search ................................ 606/139, 143, 606/144, 148, 151, 149, 213, 214, 21.1; 604/49–53, 95, 280

(56) References Cited

U.S. PATENT DOCUMENTS

| | | |
|---|---|---|
| 1,586,654 A | 6/1926 | Bierman |
| 3,769,984 A | 11/1973 | Muench |
| 3,831,607 A | 8/1974 | Lindemann |
| 3,920,021 A | 11/1975 | Hiltebrandt |
| 4,306,561 A | 12/1981 | de Medinaceli |
| 4,567,890 A | 2/1986 | Otha et al. |
| 4,685,459 A | 8/1987 | Koch et al. |
| 4,705,040 A | 11/1987 | Mueller et al. |
| 4,741,330 A | 5/1988 | Hayhurst |
| 4,819,633 A | 4/1989 | Bauer et al. |
| 4,924,864 A | 5/1990 | Danzig |
| 4,934,340 A | 6/1990 | Ebling et al. |
| 4,936,857 A | 6/1990 | Kulik |
| 4,940,064 A | 7/1990 | Desai |
| 5,026,959 A | 6/1991 | Ito et al. |
| 5,122,156 A | 6/1992 | Granger et al. |
| 5,147,357 A | 9/1992 | Rose et al. |
| 5,203,773 A | 4/1993 | Green |
| 5,215,103 A | 6/1993 | Desai |
| 5,226,429 A | 7/1993 | Kuzmak |
| 5,228,442 A | 7/1993 | Imran |
| 5,239,999 A | 8/1993 | Imran |
| 5,242,441 A | 9/1993 | Avitall |
| 5,275,162 A | 1/1994 | Edwards et al. |
| 5,290,286 A | 3/1994 | Parins |
| 5,293,868 A | 3/1994 | Nardella |
| 5,297,536 A | 3/1994 | Wilk |

(List continued on next page.)

FOREIGN PATENT DOCUMENTS

| | | |
|---|---|---|
| EP | 0584787 A1 | 3/1994 |
| WO | WO-95/05121 | 2/1995 |

OTHER PUBLICATIONS

Claims as of Apr. 9, 2004 in U.S. application Ser. No. 10/160,960 (which corresponds to US Pub. app. No. 2002/0151889 A1).

*Primary Examiner*—Kevin T. Truong
(74) *Attorney, Agent, or Firm*—Henricks, Slavin & Holmes LLP

(57) ABSTRACT

Devices for insertion into an atrial appendage of stasis reducing components such as mesh members, chemical bonding agents or expandable anchors are disclosed.

8 Claims, 17 Drawing Sheets

U.S. PATENT DOCUMENTS

| | | | |
|---|---|---|---|
| 5,300,065 A | 4/1994 | Anderson | |
| 5,306,234 A | 4/1994 | Johnson | |
| 5,318,221 A | 6/1994 | Green et al. | |
| 5,318,527 A | 6/1994 | Hyde et al. | |
| 5,318,564 A | 6/1994 | Eggers | |
| 5,322,064 A | 6/1994 | Lundquist | |
| 5,324,288 A | 6/1994 | Billings et al. | |
| 5,327,905 A | 7/1994 | Avitall | |
| 5,328,467 A | 7/1994 | Edwards et al. | |
| 5,348,554 A | 9/1994 | Imran et al. | |
| 5,354,292 A | 10/1994 | Braeuer et al. | |
| 5,354,295 A | 10/1994 | Guglielmi et al. | |
| 5,354,297 A | 10/1994 | Avitall | |
| 5,357,956 A | 10/1994 | Nardella | |
| 5,358,479 A | 10/1994 | Wilson | |
| 5,364,002 A | 11/1994 | Green et al. | |
| 5,365,926 A | 11/1994 | Desai | |
| 5,366,460 A | 11/1994 | Eberbach | |
| 5,368,599 A | 11/1994 | Hirsch et al. | |
| 5,370,650 A | 12/1994 | Tovey et al. | |
| 5,370,678 A | 12/1994 | Edwards et al. | |
| 5,374,268 A | 12/1994 | Sander | |
| 5,383,882 A | 1/1995 | Buess et al. | |
| 5,383,917 A | 1/1995 | Desai et al. | |
| 5,385,148 A | 1/1995 | Lesh et al. | |
| 5,387,219 A | 2/1995 | Rappe | |
| 5,392,978 A | 2/1995 | Velez et al. | |
| 5,392,979 A | 2/1995 | Green et al. | |
| 5,395,381 A | 3/1995 | Green et al. | |
| 5,397,331 A | 3/1995 | Himpens et al. | |
| 5,397,332 A | 3/1995 | Kammerer et al. | |
| 5,403,329 A | 4/1995 | Hinchcliffe | |
| 5,403,331 A | 4/1995 | Chesterfield et al. | |
| 5,403,342 A | 4/1995 | Tovey et al. | |
| 5,405,072 A | 4/1995 | Zlock et al. | |
| 5,405,351 A | 4/1995 | Kinet et al. | |
| 5,405,360 A | 4/1995 | Tovey | |
| 5,405,376 A | 4/1995 | Mulier et al. | |
| 5,417,691 A | 5/1995 | Hayhurst | |
| 5,443,463 A | 8/1995 | Stern et al. | |
| 5,445,638 A | 8/1995 | Rydell et al. | |
| 5,450,860 A | 9/1995 | O'Connor | |
| 5,462,561 A * | 10/1995 | Voda | 606/144 |
| 5,478,353 A | 12/1995 | Yoon | |
| 5,484,444 A | 1/1996 | Braunschweiler et al. | |
| 5,527,343 A | 6/1996 | Bonutti | |
| 5,540,684 A | 7/1996 | Hassler, Jr. | |
| 5,549,619 A | 8/1996 | Peters et al. | |
| 5,554,183 A | 9/1996 | Nazari | |
| 5,569,241 A | 10/1996 | Edwards | |
| 5,582,609 A | 12/1996 | Swanson et al. | |
| 5,599,329 A | 2/1997 | Gabbay | |
| 5,626,607 A | 5/1997 | Malecki et al. | |
| 5,693,051 A | 12/1997 | Schulze et al. | |
| 5,707,369 A | 1/1998 | Vaitekunas et al. | |
| 5,833,690 A | 11/1998 | Yates et al. | |
| 5,865,791 A * | 2/1999 | Whayne et al. | 606/194 |
| 5,984,917 A | 11/1999 | Fleischman et al. | |
| 6,132,438 A | 10/2000 | Fleischman et al. | |
| 6,161,543 A | 12/2000 | Cox et al. | |
| 6,379,366 B1 | 4/2002 | Fleischman et al. | |
| 2002/0151889 A1 | 10/2002 | Swanson et al. | |

* cited by examiner

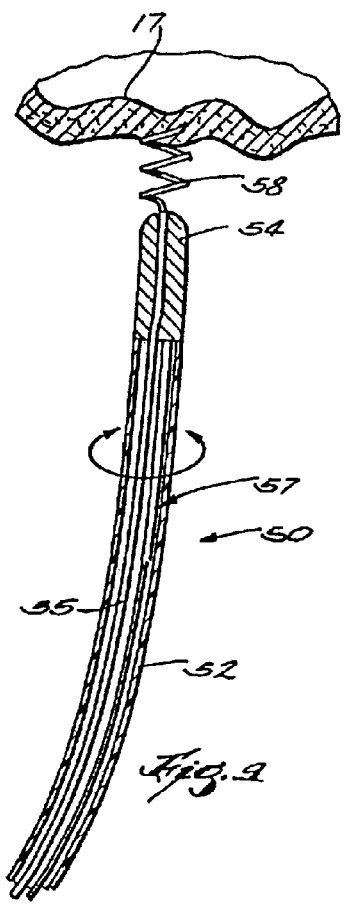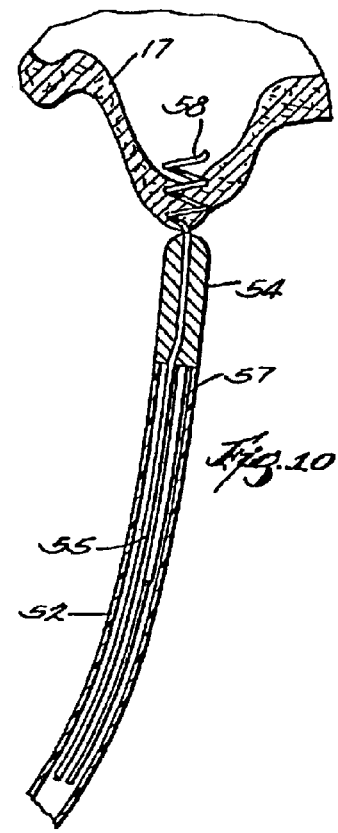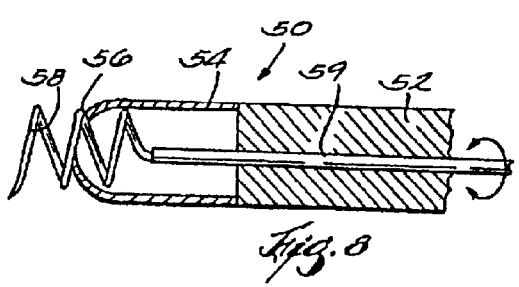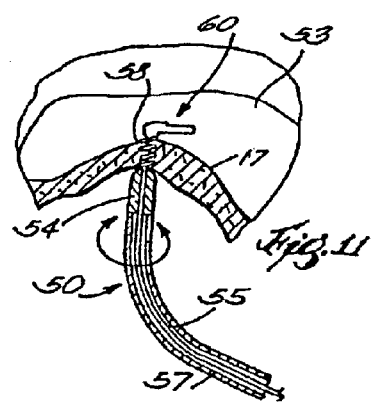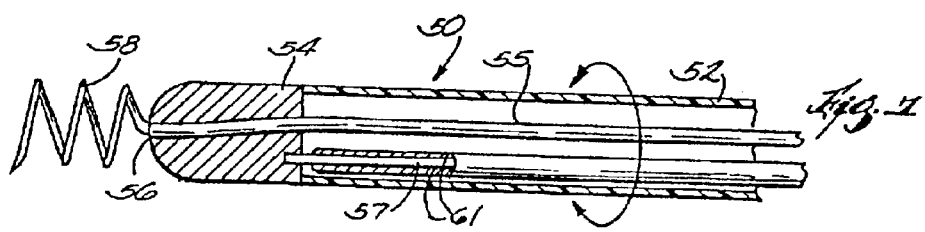

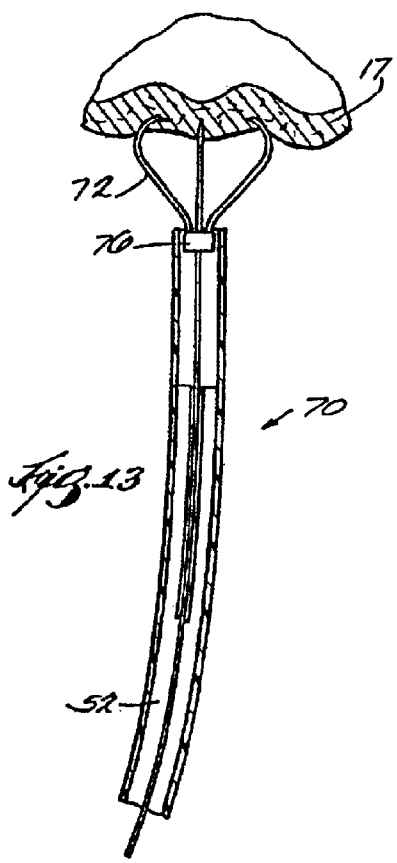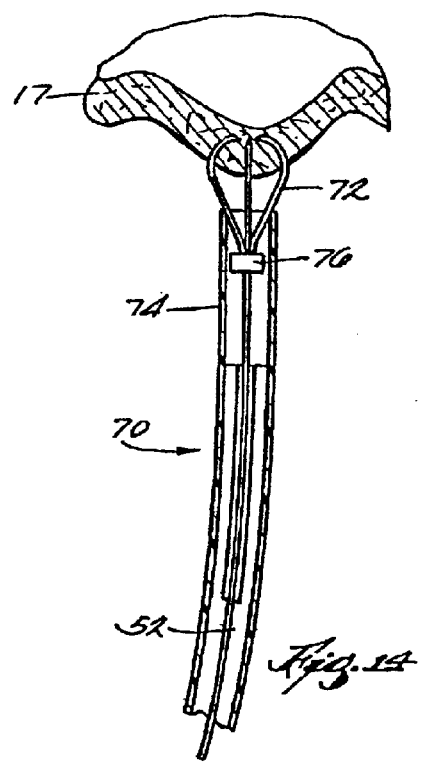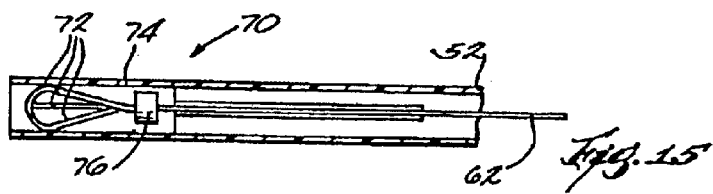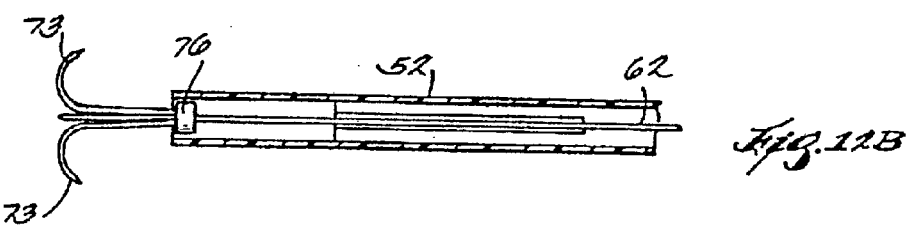

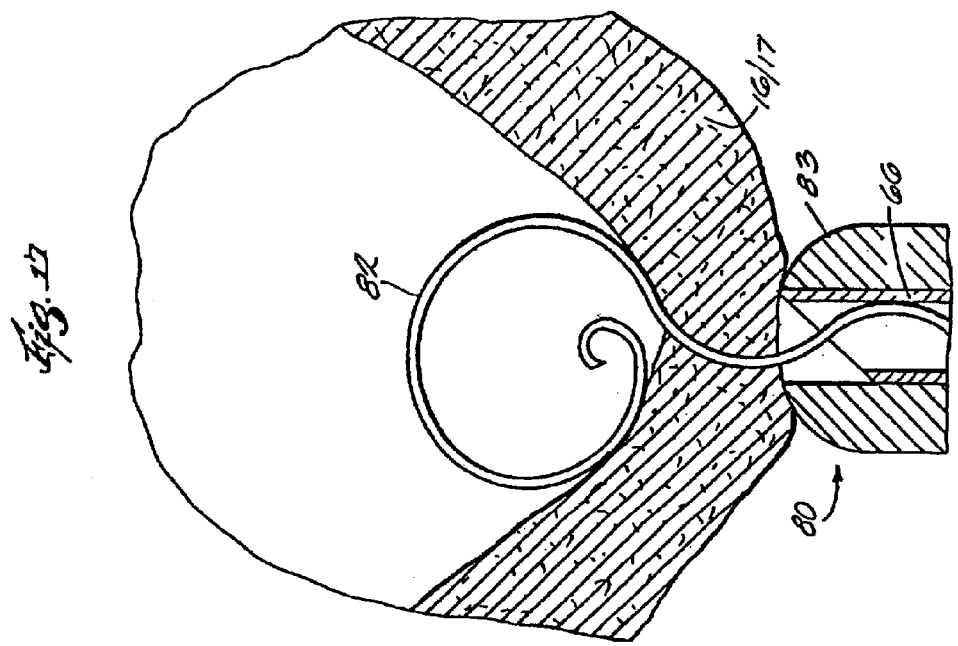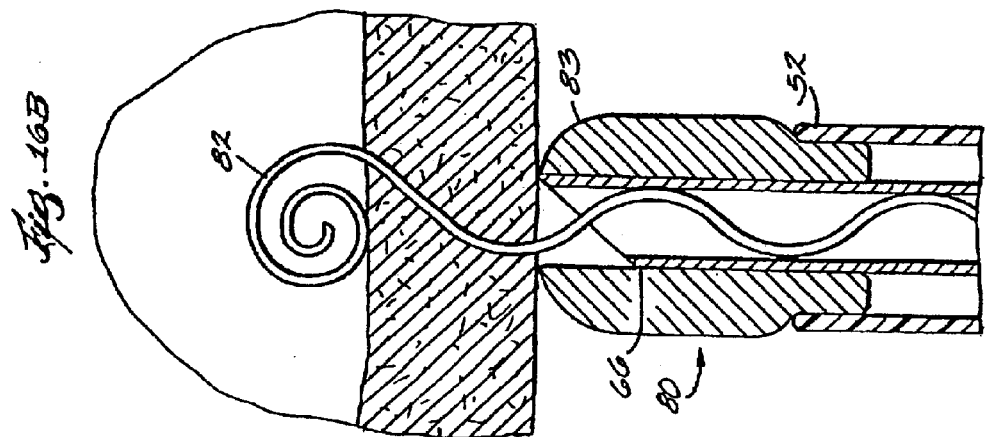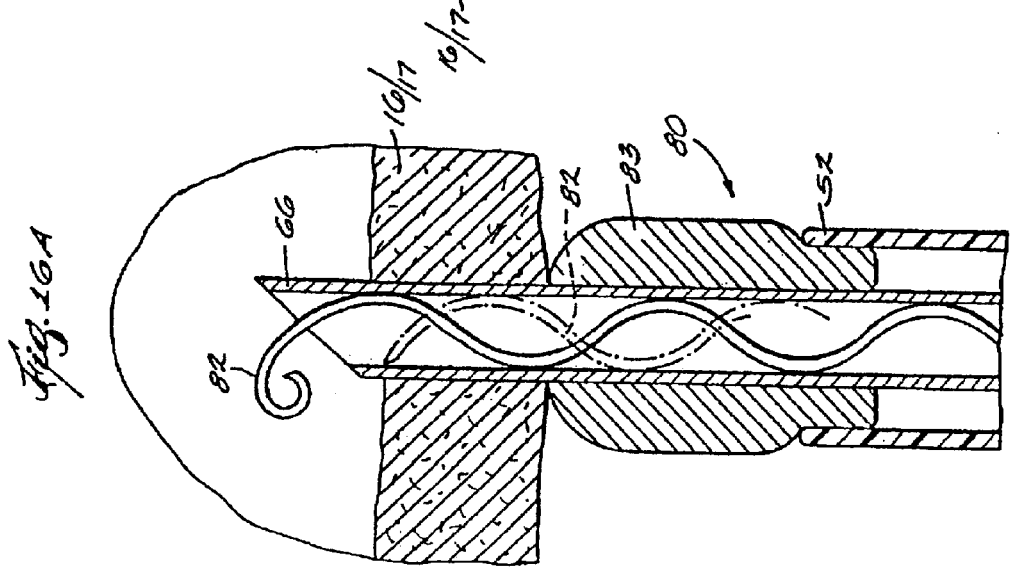

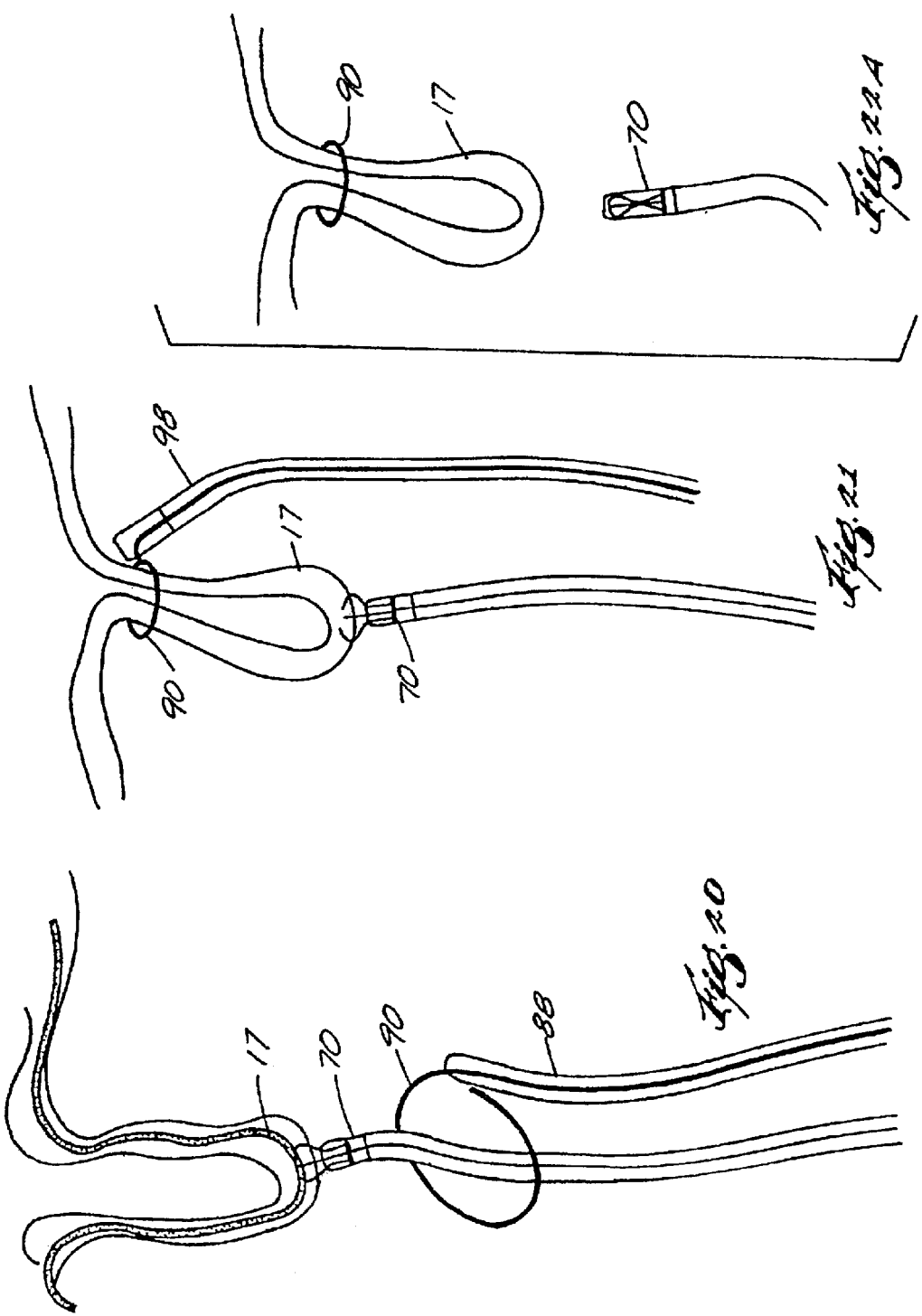

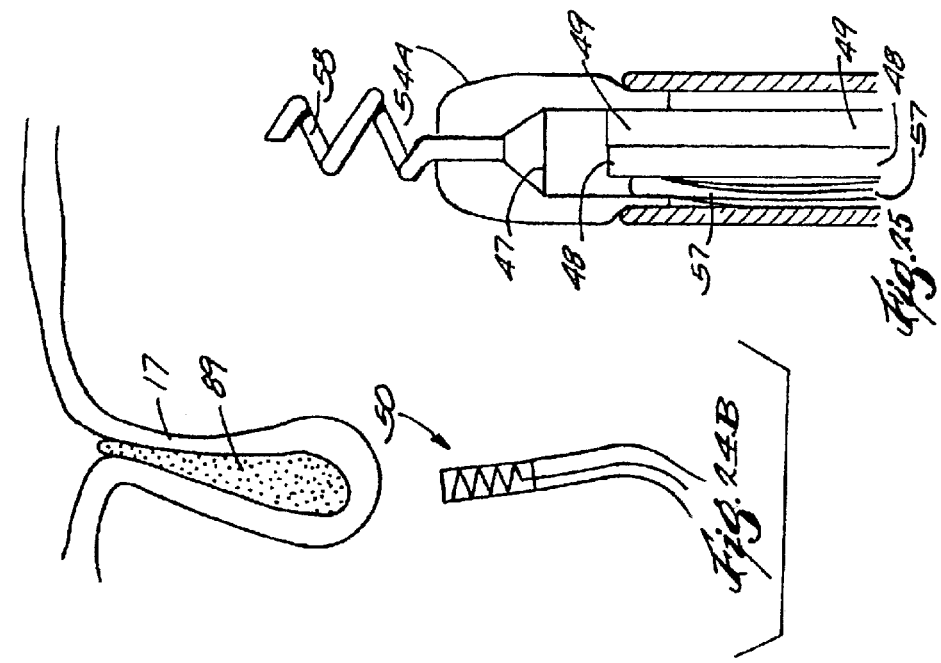
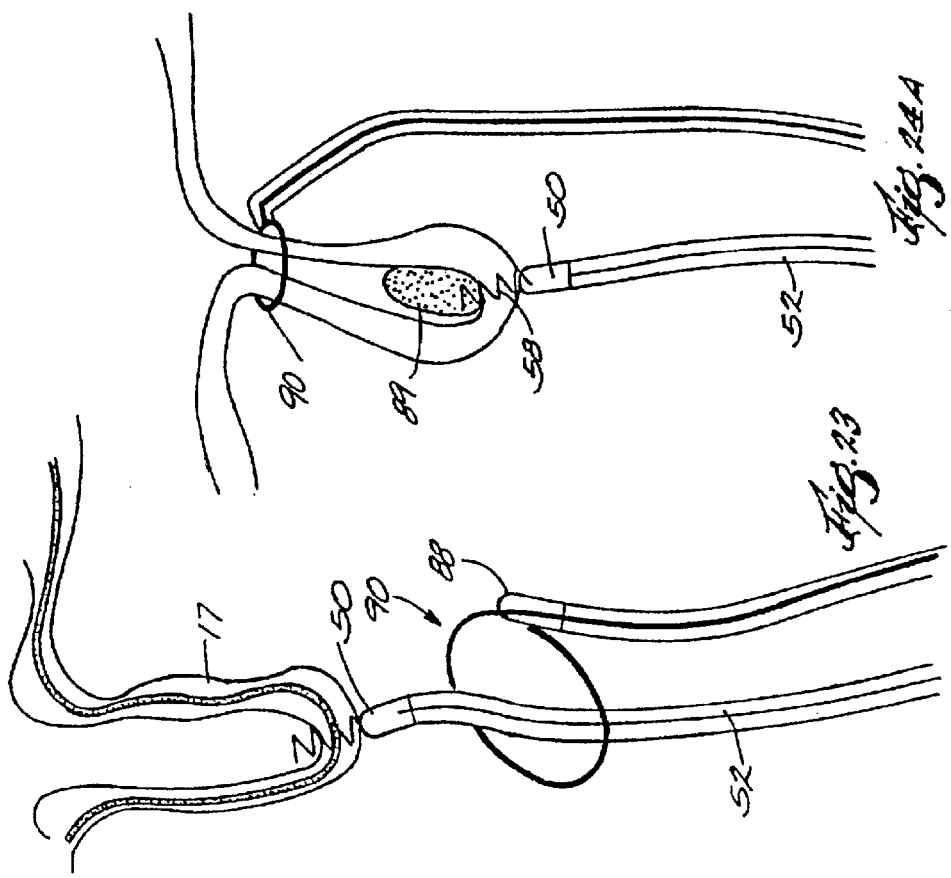

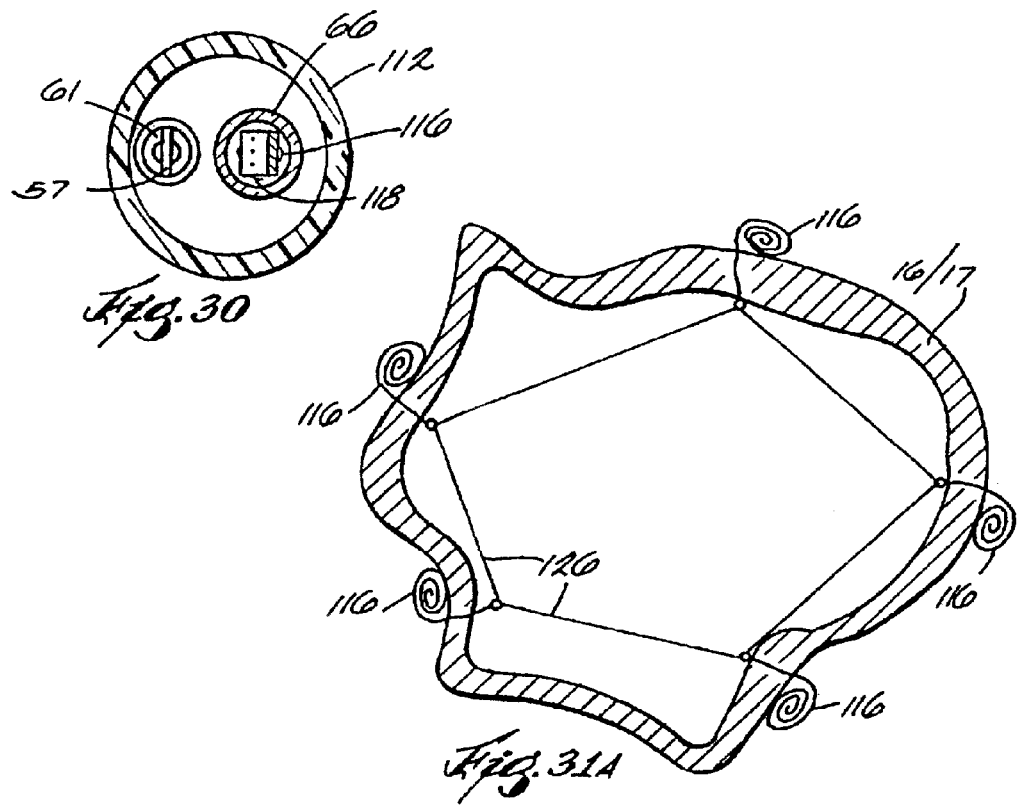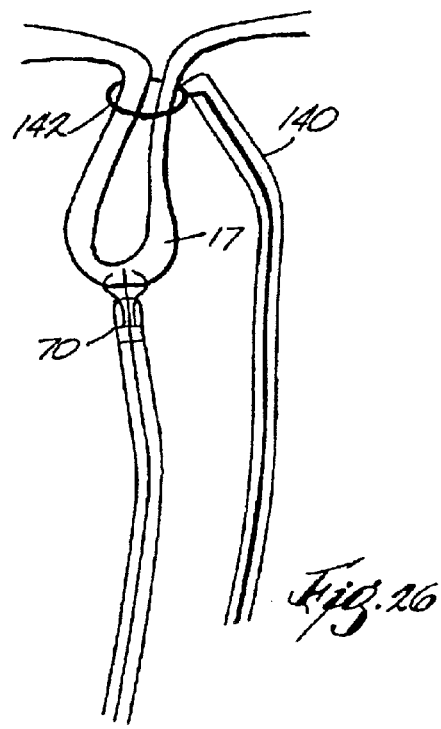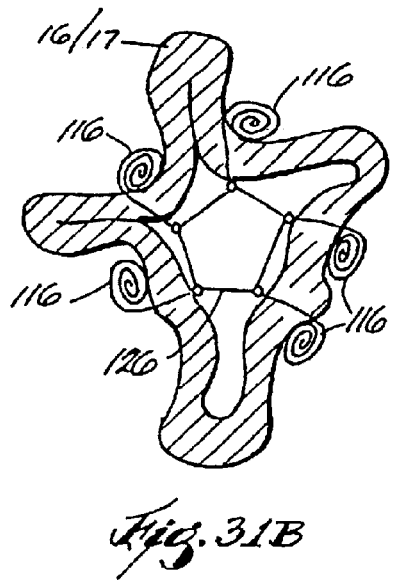

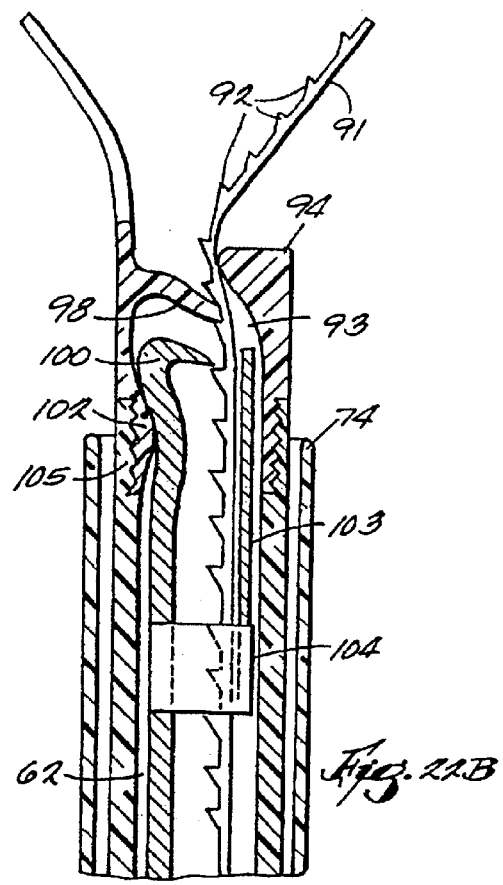
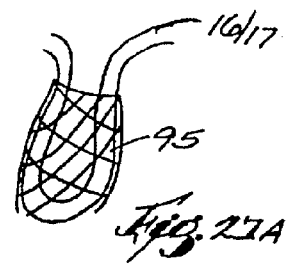
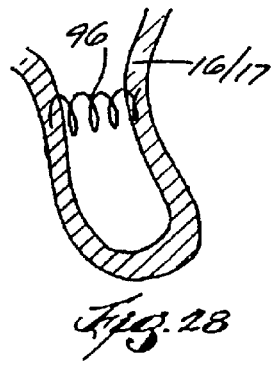
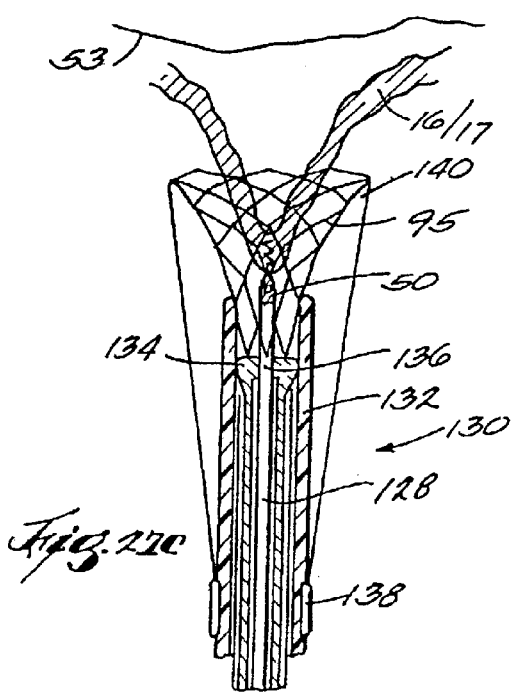
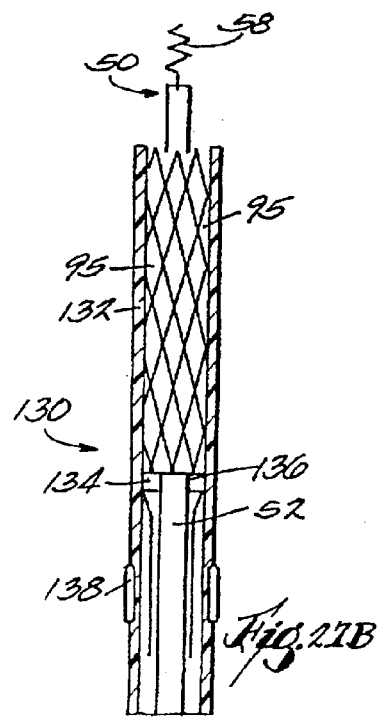

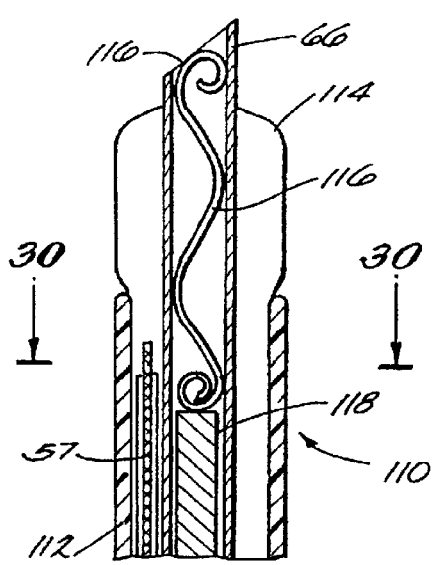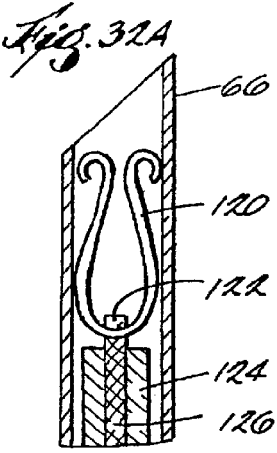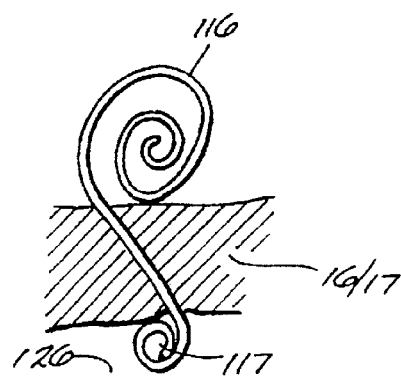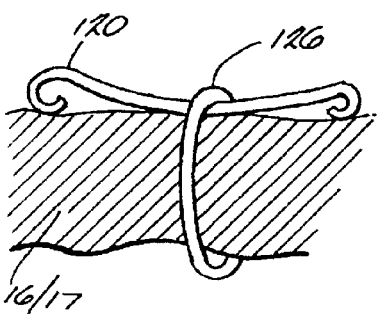

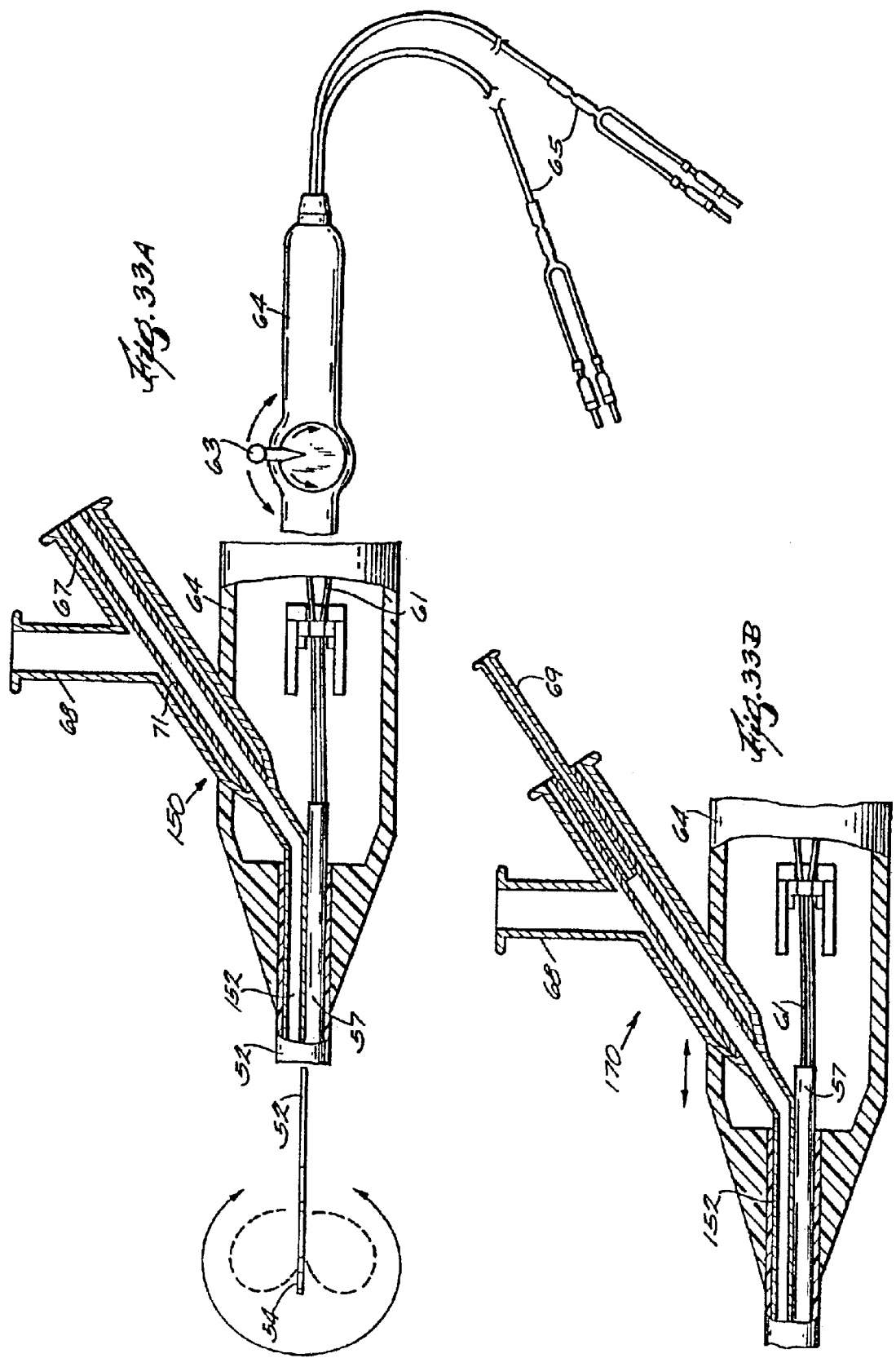

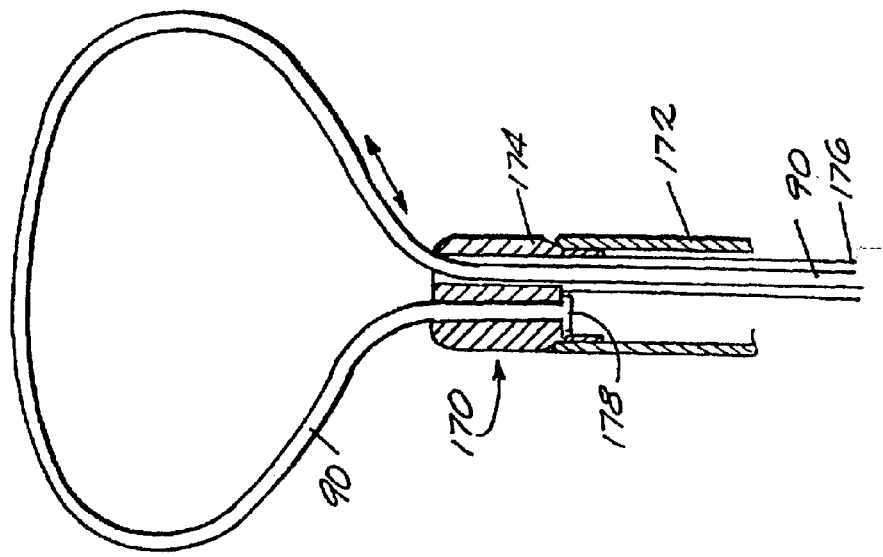
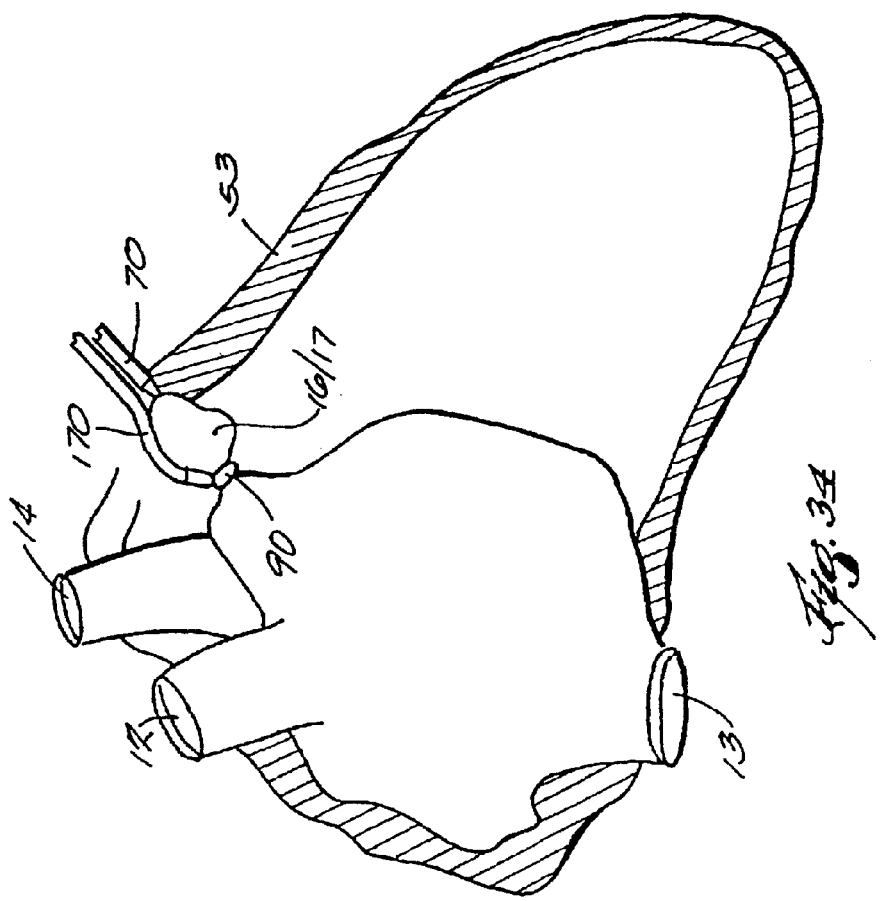

APPARATUS FOR ELECTRICALLY ISOLATING A PORTION OF THE ATRIA

This application is a continuation of U.S. application Ser. No. 09/524,263, filed Mar. 13, 2000, now U.S. Pat. No. 6,379,366, which is a continuation of U.S. application Ser. No. 08/483,991, filed Jun. 7, 1995, now U.S. Patent No. 6,132,438.

FIELD OF THE INVENTION

This invention relates to the reduction of regions of blood stasis and ultimately thrombus formation in such regions, particularly in the atrial appendages for patients with atrial fibrillation. More specifically, the invention relates to procedures and devices for affixing the atrial appendages in an orientation that reduces subsequent formation of thrombus.

BACKGROUND OF THE INVENTION

The atria must enable organized electrical propagation from the SA Node to the AV Node to stimulate the atria to contract in an organized way to transport blood from the atria to the ventricles, and to provide timed stimulation of the ventricles. The atrial appendages are especially important in the transport of blood because they have a sack-like geometry with a neck potentially more narrow than the pouch. In this case, contraction of the appendage is essential to maintain an average absolute blood velocity high enough to eliminate potential stasis regions which may lead to thrombus formation.

Atrial fibrillation and abnormalities which may lead to atrial fibrillation (such as mitral and/or tricuspid regurgitation) are often associated with abnormal electrical propagation through the heart leading to inefficient transport of blood in certain regions of the atria, and/or an enlargement of one or both atria to up to 2–3 times the normal size.

Heretofore, atrial fibrillation has often been treated either by administration of drugs or through surgical procedures, for example, procedures which surgically create a maze pattern in the atria which reduces the probability of fibrillation. The typical access points into the interior of the atria during a surgical procedure are the atrial appendages. Therefore, at the conclusion of the surgical procedure, the region occupied by the atrial appendages is eliminated by surgically removing the appendages. This mitigates subsequent problems resulting from blood stasis in the atrial appendages as well as from electrical isolation of the appendages from the rest of the atria.

More recently, maze-like procedures have been developed utilizing catheters which may create long thin lesions to effectively create a maze for electrical conduction in a predetermined path. However, such minimally invasive procedures may result in regions of continued blood stasis, particularly in the atrial appendages due to electrical isolation of the appendages or decreased contractility of the tissue due to the destruction of large regions of atrial tissue. Also, the response of the atria to permanent conversion from atrial fibrillation to sinus rhythm after a catheter-based and/or surgical maze procedure has not been proven to return appendage function to normal.

Since such catheterization procedures do not admit themselves to surgical removal of the appendages, a need has developed for procedures and devices which reduce stasis regions to effectively minimize subsequent thrombus formation within the appendages. Specifically, procedures and devices which reposition the atrial appendages and affix them in the altered position to reduce stasis regions and ultimately thrombus formation would be desirable.

SUMMARY OF THE INVENTION

An important aspect of the invention involves providing methods and devices to reposition the atrial appendages, for example by inversion thereof either totally or partially. In accordance with this aspect of the invention, several embodiments of devices are provided for grabbing or otherwise attaching themselves to an appendage wall and either inverting or otherwise pulling the walls of the appendage together to reduce the size of the region of potential blood stasis, and consequently the volume of the affected atrium. In accordance with this aspect, it is an object of the invention to reduce the region of potentially static blood and, hence the thrombogenicity of the atrium.

In accordance with one embodiment addressing this aspect of the invention, a device is provided which uses a distal helical coil to penetrate the appendage wall and, thus, provide an attachment for pulling the appendage inwardly into the atrium. In accordance with a further, alternative, embodiment, a multi-pronged grabbing device is provided on the distal end of a catheter which enables grabbing of the appendage surface with the prongs for pulling on the walls to cause an inversion thereof and/or to reduce atrial volume. In accordance with a still further alternative embodiment, a device is provided which perforates the appendage wall and then this, or another member is inserted to expand on the exterior appendage wall surface, thereby anchoring the catheter to the appendage wall so that the wall may be pulled into the atrium.

Another important aspect of the invention involves methods and devices for affixing the appendages in a predetermined position for permanent reduction of potential stasis regions. In accordance with one embodiment addressing this aspect of the invention, the appendages are chemically bonded in a predetermined position such as the inverted position. In accordance with this aspect of the invention, it is preferred that a biocompatible chemical bonding agent be introduced into the area outside of the appendages to chemically bond them in position, without bonding the epicardial surface of the atria to the pericardium. In accordance with this constraint, the chemical bonding can be assisted by utilizing an encircling tying means which may either be formed of a material designed to permanently stay in place around the appendage or, alternatively, which may be a temporary support structure for maintaining the appendage's shape during the affixing process.

Further, in accordance with this aspect of the invention, alternative devices are provided for introduction of chemical bonding agents into the area outside of the appendage epicardium. In accordance with one such embodiment, a helical grasping device is provided which uses a hollow helical coil, which thereby provides a lumen for injecting a bonding agent therethrough after the appendage wall has been penetrated by the helical device.

In accordance with an alternative embodiment related to this aspect, a separate probe is provided for introduction of a chemical bonding agent. The separate probe may take the form of a sharply pointed elongated hollow tubular canula which forms an injection port separate from the appendage surface grasping device.

In accordance with yet another alternative embodiment addressing this aspect of the invention, several alternative devices and procedures for mechanically fixing the appendages in a desired orientation are provided. In accordance with one such embodiment of the invention, an appendage encircling lasso device is utilized to encircle and affix the appendages into the desired orientation. In accordance with a related alternative embodiment, the lasso device may be of the zip-tie type which utilizes a ratcheting mechanism on the surface of the encircling material so that the lasso is of the type that can be tightened but cannot loosen once affixed in the tightened position. In accordance with a still further alternative embodiment addressing this aspect of the invention, a pre-shaped memory elastic material such as nickel titanium or a similar material may be introduced around or into the appendage and allowed to resume its shape either by elastic memory or temperature transition memory to thereby affix the position of the inverted appendage. Such devices may either be pre-shaped to encircle the inverted appendage or may be extended through the appendage walls to mechanically affix them together.

In accordance with yet another procedure for affixing the appendage walls together, there is provided a catheter having RF energy emitting electrodes which can thermally fuse the inverted appendage walls together.

In accordance with a still further alternate embodiment, a device such as a nitinol mesh is introduced into the atrial appendage interior without inversion thereof in order to form a reinforcement for anchoring thrombi in position where collagen may accumulate to fill the appendage with natural materials which are thus anchored in place so that they do not enter the bloodstream.

In accordance with a yet further embodiment of the invention, a suture material may be secured to the appendage walls, in an arrangement resembling a purse drawstring, which can be pulled together to compress the appendage walls against each other into a tightened sack where the pouch of the appendage is effectively separated from the blood pool of the atrium.

Further objects and advantages of the invention will become apparent from the following detailed description, the claims and the accompanying drawings.

BRIEF DESCRIPTION OF THE DRAWINGS

FIG. 7 is a side view illustrating a helical coil attaching catheter used in connection with the invention;

FIG. 8 is a sectional view illustrating a helical coil catheter with an independently rotatable hollow coil assembly with a lumen extending therethrough;

FIG. 9 is a sectional view showing the insertion of the helical coil catheter in FIG. 7 into the myocardium to provide a focal point for pulling the appendage;

FIG. 10 illustrates the inversion of the appendage wall shown in FIG. 9 utilizing the catheter helical coil assembly shown in FIG. 7;

FIG. 11 is a fragmentary view showing the introduction through the helical coil assembly of FIG. 7 of a marking contrast material;

FIG. 12A is a sectional view of a catheter distal tip employing a three prong attaching catheter;

FIG. 12B is a sectional view of a catheter similar to that shown in FIG. 12A except that the prongs extend radially outward;

FIG. 13 is a fragmentary view illustrating attachment of the catheter of FIG. 12A to an appendage wall;

FIG. 14 is a fragmentary view illustrating use of the catheter of FIG. 12A for inversion of an appendage wall;

FIG. 15 is a fragmentary view of the distal tip of the catheter of FIG. 12A retracted into a protective sheath;

FIG. 16A is a fragmentary side view of a catheter distal section illustrating a hollow needle incorporating an internal extending, expandable type attachment/pulling element;

FIG. 16B is a side view of the attachment/pulling element of FIG. 16A in an expanded configuration;

FIG. 17 is a fragmentary view illustrating another attachment/pulling element configuration which may be used to provide an attachment point with which to invert an atrial appendage;

FIG. 20 is a fragmentary side view showing the use of a grasping catheter of the general type shown in FIG. 12A in conjunction with a lasso catheter for maintaining the walls of the inverted appendage together;

FIGS. 21 and 22A are fragmentary views of the combination shown in FIG. 20 illustrating further steps of tying the appendages in an inverted orientation;

FIG. 22B is a schematic showing one embodiment of a tying mechanism for use in the lasso catheter of FIGS. 20–22A;

FIGS. 23 and 24A are fragmentary views illustrating the use of a catheter of the general type shown in FIG. 7 in conjunction with a releasable lasso catheter and showing the introduction of a biocompatible adhesive/filler material into the space outside of the inverted appendage;

FIG. 24B is a fragmentary view showing the withdrawal of a catheter of the type shown in FIG. 7 after affixing in place an inverted appendage with a stabilizing filler material;

FIG. 25 is a fragmentary sectional view showing a catheter with dual infusion ports for introduction of fluid materials;

FIG. 26 is a fragmentary view showing the use of a further embodiment of a lasso catheter, which is made of a metallic coil or other electrical conductor and is connected to an RF Generator for use in thermally fusing the appendage walls;

FIG. 27A is a fragmentary view showing the application over an inverted appendage of a metallic mesh;

FIGS. 27B and 27C are fragmentary sectional views of a catheter mechanism used to expand the metallic mesh during insertion over the inverted appendage;

FIG. 28 is a fragmentary sectional view showing the insertion of a helical metallic winding made from a memory transitional material which upon introduction through the appendage expands or contracts to its original form at body temperature and holds the appendage in place;

FIG. 29 is a sectional view of a catheter containing an expandable anchor for insertion into an inverted appendage;

FIG. 30 is a cross-sectional view taken along 30—30 of FIG. 29;

FIG. 31A is a cross-sectional view of an appendage showing the use of insertable expandable anchors in conjunction with a draw string;

FIG. 31B is a cross-sectional view showing the appendage of FIG. 31A after it has been drawn together;

FIG. 31C is a cross-sectional view showing a single expandable anchor inserted into an appendage wall;

FIG. 32A is a sectional view of a catheter containing an alternative type of expandable anchor for insertion into an inverted appendage;

FIG. 32B is a cross-sectional view showing a single expandable anchor of the type shown in FIG. 32A inserted into an appendage wall;

FIG. 33A is a side view of a handle mechanism for a catheter with a fixed hollow needle and an access point for an internal stylet mechanism;

FIG. 33B is a side view of a handle mechanism for a catheter with a moveable hollow needle and an access point for an internal stylet mechanism;

FIG. 34 is a fragmentary view, with parts in section, illustrating introduction of a catheter into pericardium by means of a thoracostomy in accordance with the invention; and, FIG. 35 is an enlarged fragmentary view, with parts in section, of one embodiment of a catheter usable in the procedure shown in FIG. 34.

DETAILED DESCRIPTION OF THE ILLUSTRATED EMBODIMENTS

Figure 1:
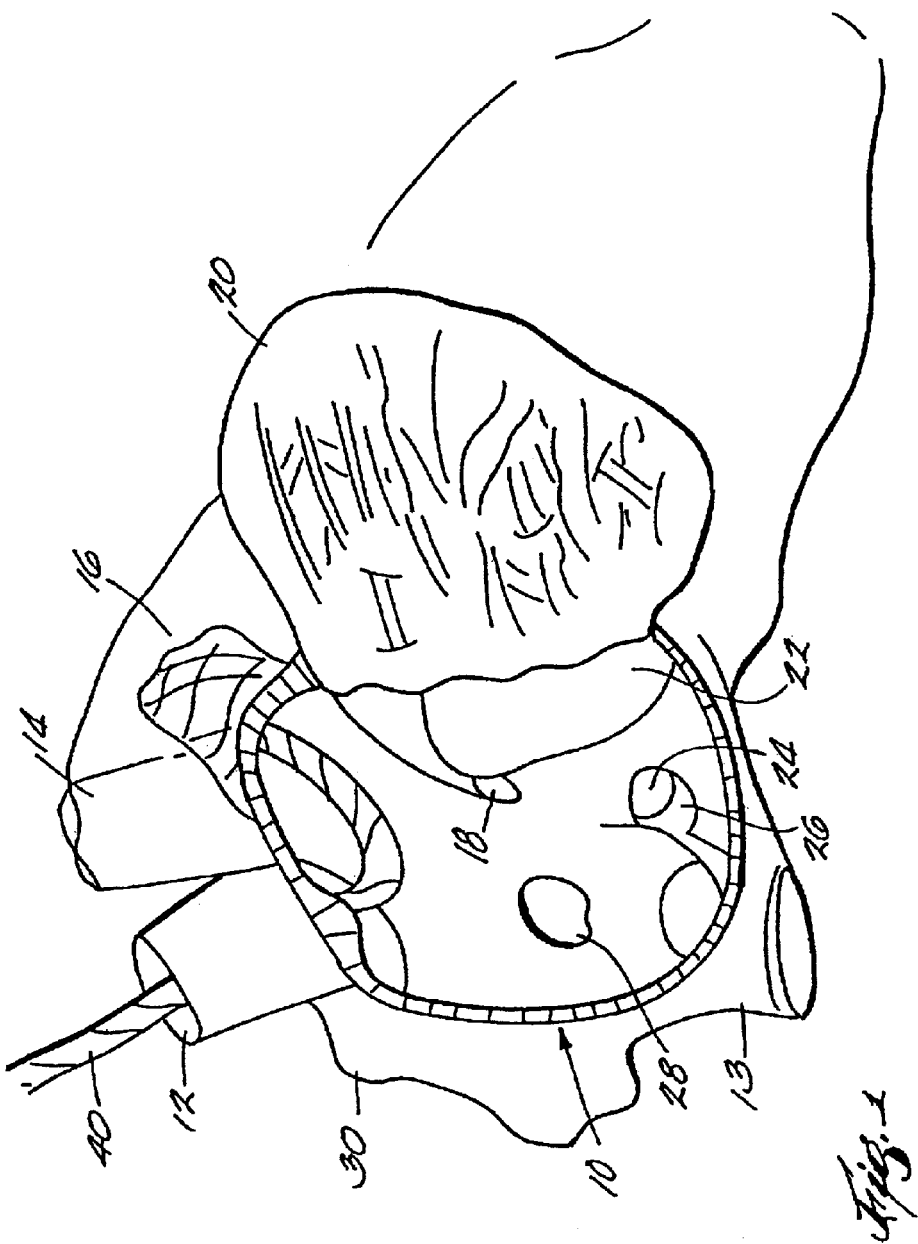
FIG. 1 is a fragmentary view, with parts in section, illustrating introduction of a catheter into the right atrium of a heart in accordance with the invention.
Figure 2:
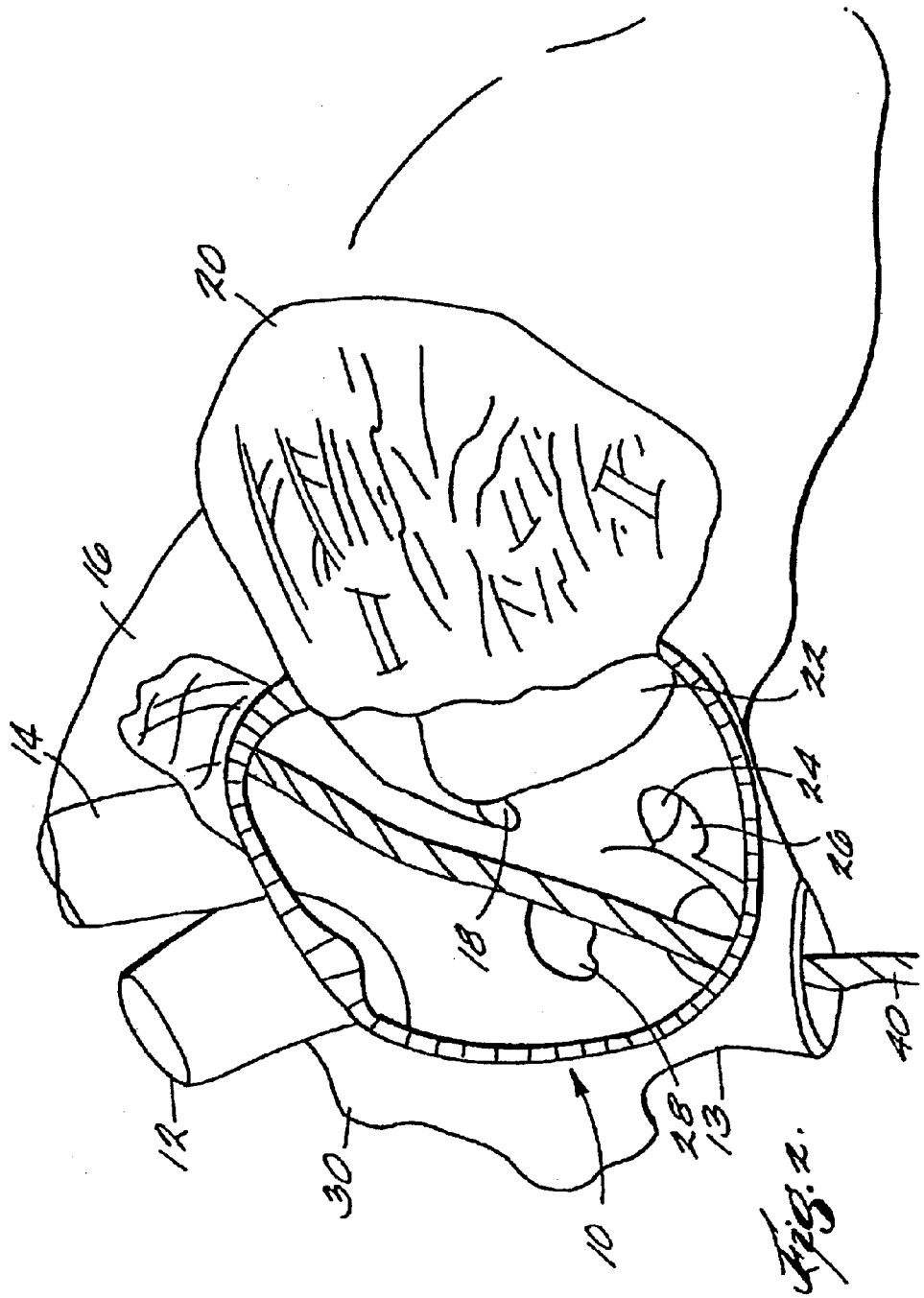
FIG. 2 is a fragmentary view, with parts in section, showing introduction of a catheter into the right atrium of the heart via the femoral vein.
Figure 3:
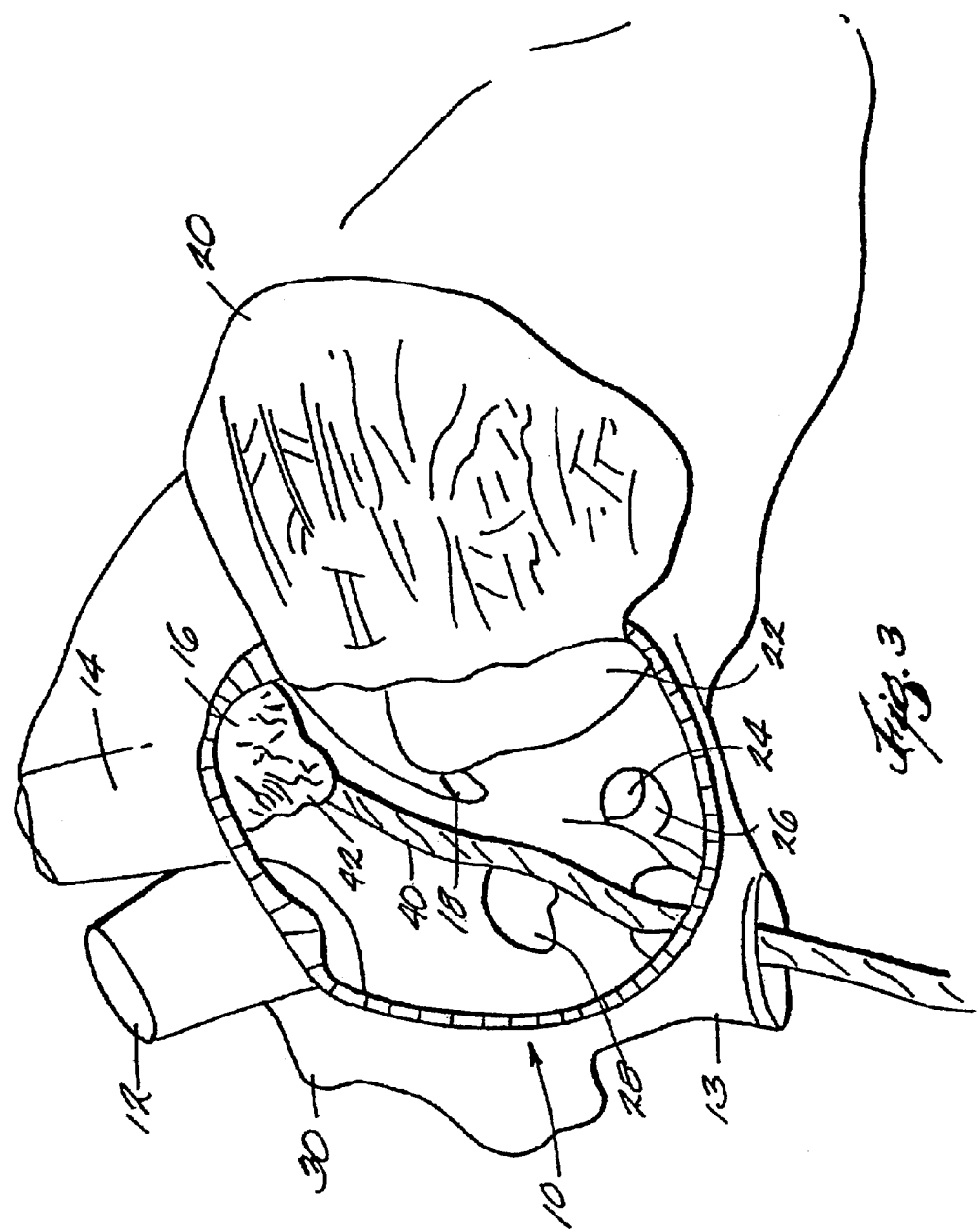
FIG. 3 is a fragmentary view showing the right atrium with the catheter introduced therein and with the right atrial appendage inverted.

Referring more specifically to the drawings, FIGS. 1–3 show, in fragmentary fashion, the right atrium 10, the superior vena cava 12, the inferior vena cava 13, the ascending aorta 14, the right atrial appendage 16, the membranous septum 18, the right atrial freewall 20, the tricuspid valve 22, the opening of the coronary sinus 24, the valve of the coronary sinus 26, and the fossa ovalis 28.

Figure 4:
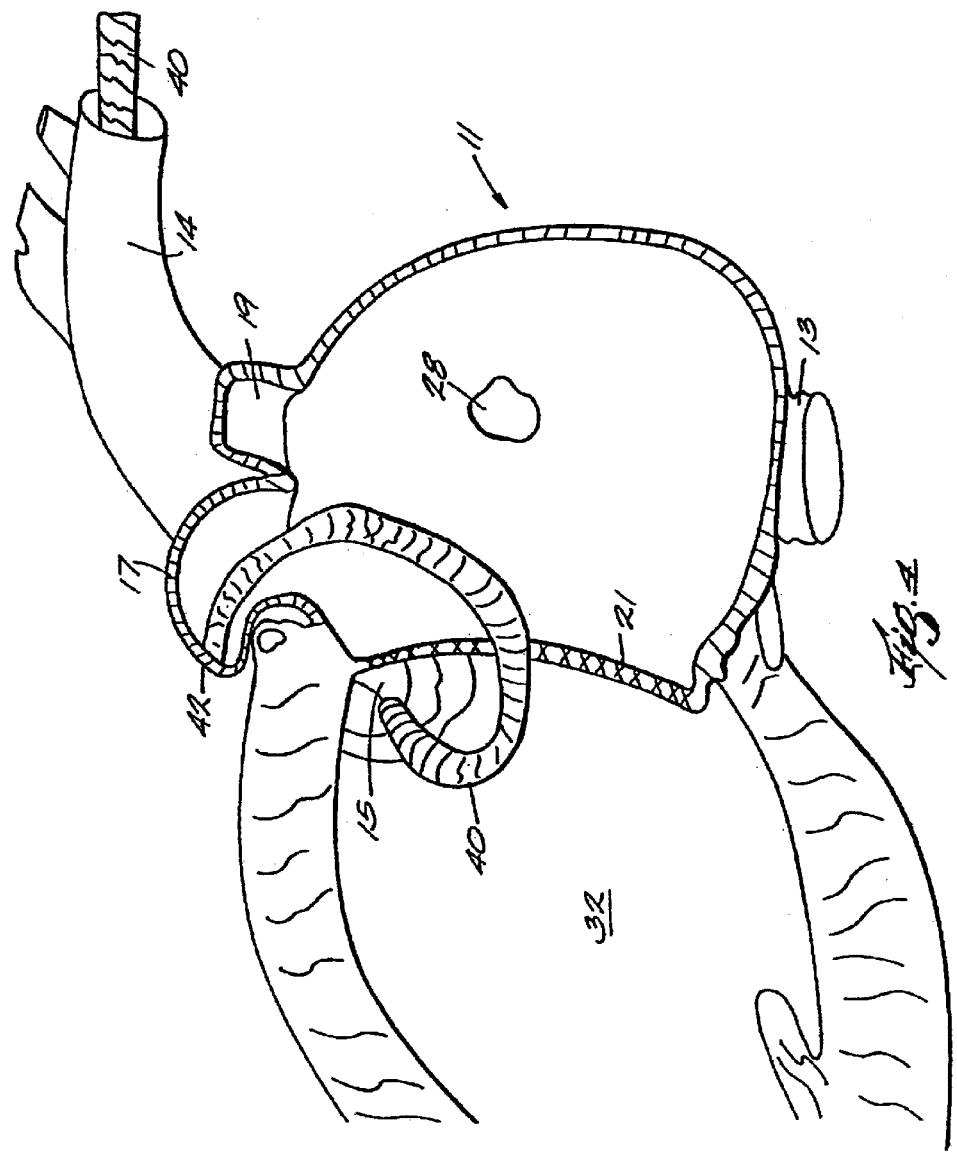
FIG. 4 is a fragmentary view of the left atrium, with parts in section, illustrating introduction of a catheter into the left atrial appendage via a retrograde procedure.
Figure 5:
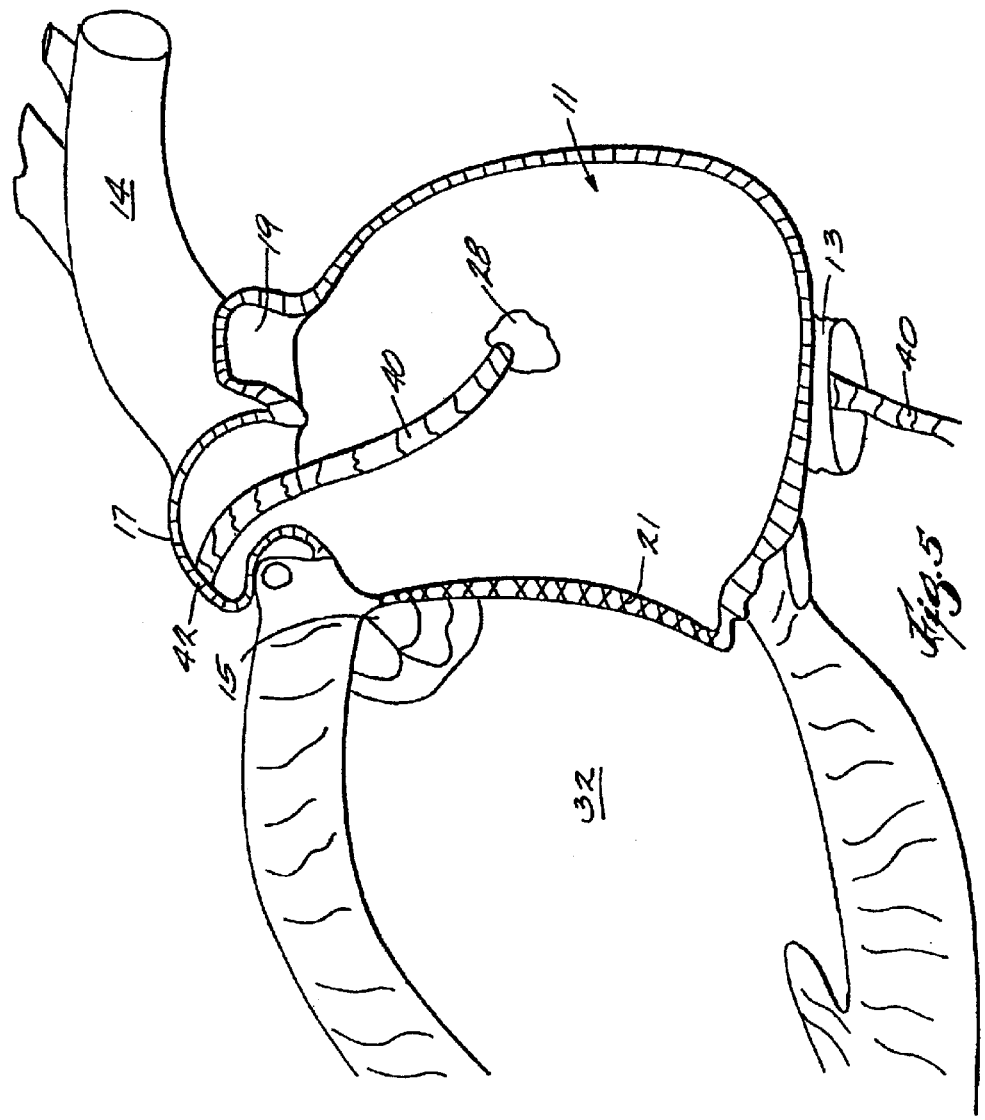
FIG. 5 is a fragmentary view, with parts in section, showing positioning of a catheter on the endocardial surface of a left atrial appendage using a transeptal procedure.
Figure 6:
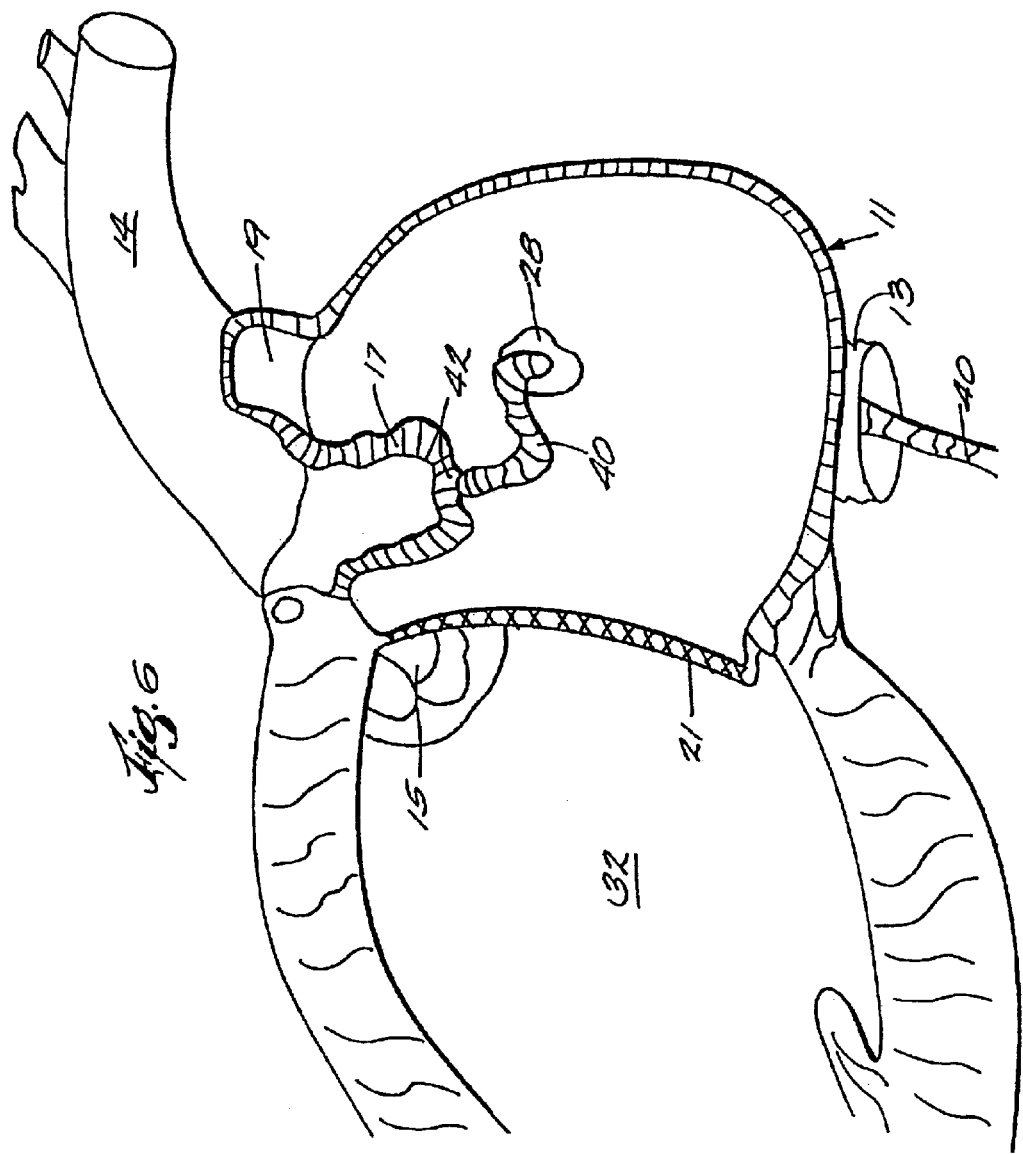
FIG. 6 shows introduction of a catheter via a transeptal approach for inversion of the left atrial appendage.

A left atrium 11 is shown in FIGS. 4–6. There are also seen therein the aortic valve 15, the left atrial appendage 17, the left superior pulmonary vein 19, the mitral valve 21, and the left ventricle 32.

A catheter 40 is shown generally being introduced into the atria of a heart through various cardiovascular introduction passageways as will be discussed hereinafter. The point of attachment of catheter 40 to the wall of an atrial appendage 16 or 17 is indicated generally at 42.

Referring to FIGS. 1–6, various ways of entering a heart chamber and positioning a catheter tip on the interior wall of the atrial appendages are illustrated. In FIG. 1, a catheter 40 is shown being advanced through the jugular vein past the superior vena cava 12 and into the right atrium 10 where it is steered so the tip is positioned on the endocardial surface of the right atrial appendage 16 where attachment is made. FIG. 2 illustrates a procedure for introducing the catheter 40 through the femoral vein into the right atrium 10 and then into the right atrial appendage 16. FIG. 3 illustrates the inversion of the right atrial appendage 16 using the catheter 40 introduced as shown in FIG. 2.

FIG. 4 illustrates the positioning of a catheter distal tip at a point 42 on the endocardial surface of the left atrial appendage 17 utilizing a retrograde procedure. A sheath with a preformed configuration may be required to maneuver the catheter tip down through the aorta 14 and up through the mitral valve 21. In addition, such a sheath would provide additional support for maneuvering the tip of the catheter. FIG. 5 shows positioning of a catheter tip at a point 42 on the endocardial surface of the left atrial appendage 17 utilizing a transeptal introduction. Transeptal introduction is achieved by inserting an introducer or sheath with an internal dilator through the femoral or jugular vein and into the interior of the right atrium. Once in the right atrium, a long hollow needle with a preformed curve and a sharpened distal tip is introduced through the dilator and is forcibly inserted through the fossa ovalis 28. A radiopaque contrast material is injected through the needle to ensure the needle is in the left atrium as opposed to being in the pericardial space, aorta, or other undesired location. Once the position of the needle in the left atrium is confirmed, the dilator and sheath are advanced over the needle and into the left atrium. Then, the needle and dilator are removed leaving the sheath as an access point to the left atrium. FIG. 6 shows the inversion of the left atrial appendage 17 after catheter 40 has been attached at point 42 and by using a transeptal approach as shown in FIG. 5. The use of such delivery systems as sheaths is shown in pending U.S. application Ser. No. 08/136,218, filed Oct. 14, 1993, and entitled "Cardiac Mapping and Ablation Systems."

Methods & Devices for Repositioning Appendage Walls

Referring now to FIGS. 7–11, there is seen one type of catheter 50 provided for attachment of the distal tip thereof to the wall of an atrial appendage 16 or 17. The catheter 50 includes a catheter body 52 having a distal tip portion 54. In this embodiment a hollow coil 58 is attached to the catheter distal tip 54 and has a lumen 55 extending from the proximal end of the coil at the distal tip attachment point to the catheter handle assembly (not shown), The coil 58 is rotated by torquing the catheter body 52. The catheter body 52 may be provided with a steering mechanism 57, for example, of the type shown in Lundquist and Thompson U.S. Pat. No. 5,254,088, which is incorporated herein by reference.

In the embodiment shown in FIG. 8 the distal tip portion 54 of the catheter 50 is provided with an opening 56 through which the helically coiled distal tip element 58 can be advanced by rotation. Upon rotation of an inner supporting member 59 relative to catheter body 52, the distal helical tip portion 58 is rotated into the wall of atrial appendage 16 or 17. This opening 56 may constitute a single isolated hole which fits only the outer diameter of the helical coil assembly or a larger hole in the distal portion of the tip. An isolated hole provides support for the helical coil assembly during advancement and withdrawal as well as providing a blunt surface masking the sharp distal tip needle 58 during manipulation of the catheter through the vasculature.

As shown in FIG. 7, the helical coil may alternatively be permanently attached to the distal tip of the catheter thus requiring rotation of the catheter body 52 to screw the helical coil into or out of the tissue.

The distal tip of the helical element 58 is sharpened so that it has the capability of impaling the tissue wall. The rotatable supporting member 59 constitutes separate torque assembly that can be rotated manually from a point outside the body to cause rotation of element 59 relative to the catheter body 52. This rotatable supporting member may be made of braided composite assembly such as stainless steel braid with polyamide, or a slotted hollow tube with an outer layer of shrink tubing. Once the helical coil assembly 58 is screwed into the appendage 16 or 17, the appendage may be pulled into the inverted position by applying pulling forces to the catheter body 52.

Since the distal helical member 58 is preferably hollow and attached to a tube with an internal lumen passing from the distal tip to the handle assembly, radiopaque contrast material 60 may be injected to detect the location of the distal tip of catheter 50 using, for example, fluoroscopy. This is important so as to ensure that the distal end of the helical coil needle 58 is in the pericardial space and has not perforated the pericardium 53 as shown in FIG. 11. In addition, the helical coil assembly and/or the distal catheter tip may be radiopaque.

Alternatively, an echoluscient material may be injected to locate the distal tip using transthoracic, transesophageal, and/or intracardiac echocardiography. Also, transponders may be attached to the helical coil assembly for locating thereof by echocardiography.

The hollow lumen 55 in the distal helical member 58 can also be used for introduction of an adhesive or bonding material therethrough as will be further set forth hereinafter.

Referring to FIGS. 12–15, there is seen an alternative type of grasping catheter 70 provided on a catheter body 52. The catheter tip 74 includes a plurality of grasping prongs 72 which are movable from an expanded position to a retracted position as seen in FIGS. 13–14 for grasping the wall of the atrial appendage 16 or 17, so that pulling forces can be applied for inversion thereof. Preferably, the pronged tips are enclosed in a tubular tip 74 which facilitates introduction of the catheter through the vasculature and into a heart chamber and subsequent withdrawal thereof once the procedure is completed. Prongs 72 are preferably mounted in a mounting block 76 in such a fashion that they are biased toward the expanded position shown in FIGS. 12A and 13. This block 76 is connected to a handle assembly through a stylet 62. As the stylet 62 is retracted at the handle, the block 76 is withdrawn into tubular tip 74; the prongs are caused to contact the interior surface of the tip 74 and move toward each other, thus impaling the surface of the appendage 16 or 17 as seen in FIG. 14. The prongs are provided with sharp distal ends to readily penetrate tissue and with a wide section at the apex of the curvature to contact a larger amount of tissue thus forming a large surface with which to pull tissue. The appendage 16/17 is then inverted by pulling the catheter body sufficiently to cause inversion. The prongs can subsequently be released by distal extension of the stylet 62 and the block 76 thereby allowing the prongs to expand again to the position shown in FIG. 13. After the prongs 72 are withdrawn from the wall of appendage 16 or 17, they can be returned to the compact position shown in FIG. 15 so the catheter may be withdrawn from the vasculature.

Alternatively, as shown in FIG. 12B, prongs 73 are provided which in the expanded form extend radially outward. During introduction of this embodiment into the appendage 16/17, the prongs 73 are collapsed into a low profile and once they have passed through the appendage wall 16/17 or inside the myocardium, the stylet 62 and thereby the block 76 is extended, allowing the prongs 73 to expand from the low profile necessary for insertion to a radiating outward profile which provides a surface with which to pull the appendage 16/17.

Yet another form of catheter attachment and pulling mechanism 80 is shown in FIGS. 16A, 16B and 17. In accordance with this embodiment, a radially expandable flexible member 82 is positioned within a hollow needle 66 located inside the interior of the catheter body 52 and distal tip element 83. Member 82 is attached to stylet 62 which extends from the distal tip 83 to the handle assembly. Flexible member 82 may be made from a memory elastic material such nickel titanium or stainless steel 17/7. More than one flexible member 82 may be attached to a stylet 62, if desired, to increase the surface provided for pulling on the appendage 16/17.

Externally operable control means, such as extendable/retractable proximal knobs, are provided for advancing the stylet 62 and hollow needle 66 independently of one another. Preferably, the distal end of the hollow needle 66 is extended through the appendage 16/17 and accesses the pericardial space. As previously described, a contrast material may be injected to confirm the location of the distal tip of hollow needle 66. Then, the stylet 62 is advanced thereby expelling the flexible member 82 and allowing it to expand from the position shown in FIG. 16A to that shown in FIG. 16B. The distal tip of the hollow needle 66 is provided with a sharpened point suitable for penetration of the appendage wall 16/17 when the flexible member 82 is in the retracted position. Then, after penetration of the wall 16 or 17, the flexible member 82 expands into its predetermined shape and the catheter is thereby attached to the wall as seen in FIG. 16B. In this position, a substantial pulling force can be applied to the atrial appendage 16 or 17 to cause inversion of the same.

The hollow needle 66 may be retracted into its retracted or resting position in element 83 to minimize any damage the sharp distal needle tip may cause while pulling the appendage 16/17. In addition, the flexible member 82 may be coiled at its distal end to prevent perforation of the tissue especially that of the pericardium while manipulating the member 82 by means of stylet 62. In an alternative embodiment, the member 82 can have a blunt end instead of a coiled tip. In FIGS. 16 & 17, the member 82 is attached to the stylet 62. An alternative configuration of the flexible member 82 (fully expanded) is shown in FIG. 17.

A number of additional shapes not shown in the FIGURES can function as member 82. Any flexible self-expanding member or configuration which may be extended into a low profile to fit inside a hollow needle or a catheter body and when extended beyond the distal end of the constraining tube will expand, may be used to provide an attachment point to pull the appendage 16/17 into an inverted position.

To retract the flexible member 82 from the attachment point 42, the sharpened hollow needle 66 is reinserted into the tissue to the proximal surface of the tissue and the flexible member 82 is removed by pulling the stylet 62. Thereafter, the hollow needle 66 and flexible member 82 are positioned in their retracted positions so the catheter may be safely removed from the vasculature. The handle 64 shown in FIGS. 33A and 33B can be used for this purpose. The rod 69 can be removed from the assembly shown in FIG. 33B and a stylet 62 and flexible member 82 substituted therefor.

Methods & Devices for Affixing the Inverted Appendages

Figure 19B:
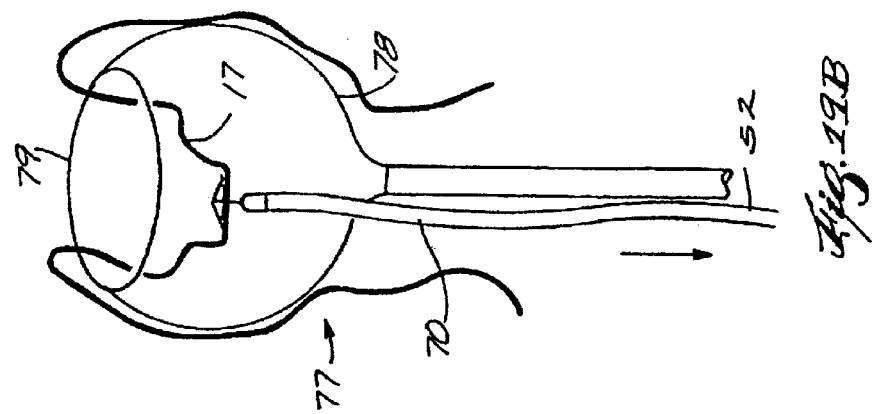
FIG. 19B is a fragmentary side view illustrating the inversion of an atrial appendage utilizing the devices shown in FIG. 19A.
Figure 19A:
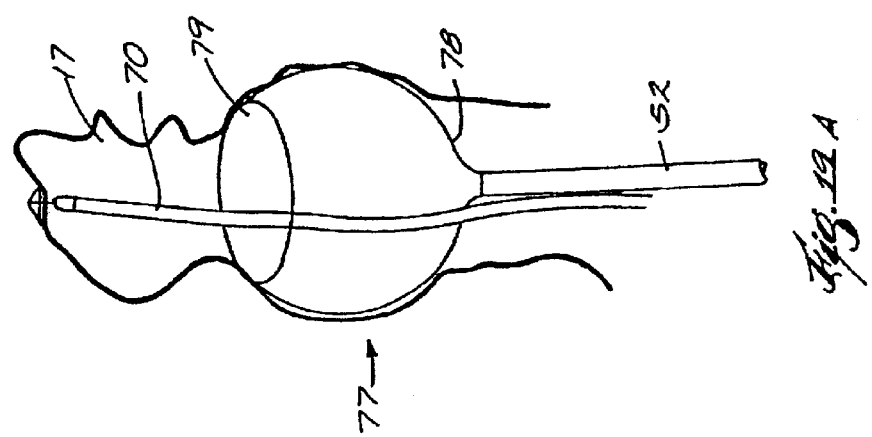
FIG. 19A illustrates an inverting catheter used in conjunction with a compound loop support catheter.
Figure 18:
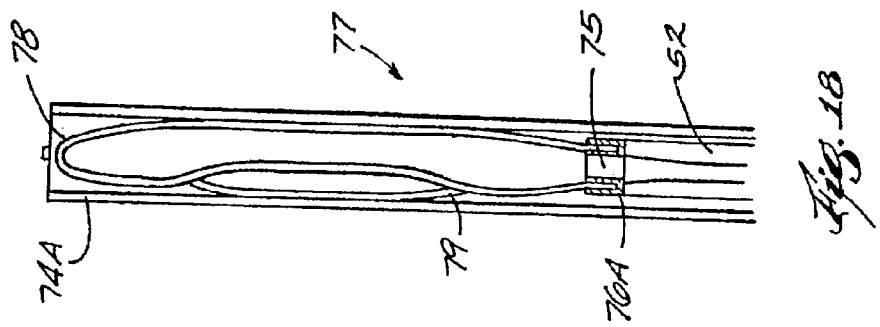
FIG. 18 is a fragmentary view showing a catheter distal tip carrying a compound loop device.

Referring to FIGS. 18, 19A and 19B, there is shown a compound loop assembly 77 carried on the distal end of a catheter 52. Loop assembly 77 may be used as a support structure for pulling therethrough of appendage 16 or 17. As seen in FIG. 18, assembly 77 is housed in an introducer sheath 74A. An extendable/retractable support block 76A is manipulated by extension and retraction of catheter body 52 relative to sheath 74A. A central opening 75 in support block 76A allows for introduction of a separate attachment catheter, for example, catheter 70 through the central lumen of catheter 52. One or more supporting splines 78 are attached to block 76A and support another loop 79 which is of a size adapted to encircle the appendage 16/17 when inverted as shown in FIG. 19B. In the embodiment of FIGS. 19A AND 19B, catheter 70 is introduced separately from catheter 52.

This compound loop assembly 77 provides a support structure to appropriately deform the atrial appendage into a necked pouch to facilitate subsequent attaching methods as described below. Any of the attaching catheters described above may be used in conjunction with the compound loop structure. The compound loop catheter 77 may contain multiple loops to enable pulling of the appendage 16/17 into multiple small inverted sections of tissue instead of one larger inverted section.

An alternative support structure, which may also be used itself to fix inverted appendage tissue in an altered position is shown in FIGS. 20–22. Here there is seen the use of a dual catheter system including a tying catheter 88 which inserts a lasso member 90 around a grasping catheter 70, which is shown for purposes of illustration. In FIGS. 20–22A, the appendage 16 or 17 is shown in the inverted position. Subsequently, the lasso member 90 is elevated around the inverted appendage 16 or 17 and thereafter tied by pulling the free end of the lasso member 90 by means of a stylet 62, which extends proximally into a handle assembly. Lasso member 90 is thus formed into a tightened configuration which holds and assists in moving the inverted appendage 16 or 17 into the position shown in FIG. 22A.

FIG. 22B shows one embodiment of a lasso member 91 which has a ratcheting mechanism to permanently tighten when the member 91 is pulled by the operator. In this case teeth 92 are adapted to slide through a slot 93 in a direction which allows tightening of the lasso, but does not allow loosening thereof. After the lasso member 91 has been tightened to maintain the position of the inverted appendage 16/17, the lasso member 91 is cut, leaving the tightened lasso in place. As seen in FIG. 22B, the lasso 91 is compressed to fit within an introducer sheath 74 for introduction into the atrium. The lasso 91 is formed in a size sufficient to encircle the inverted atrial appendage. As seen, slot 93 is formed as a constriction between an anchoring member 94 and an opposed finger 98 which engages ratchet projections 92. Finger member 98 as seen in FIG. 22B allows the ratchet projections to slide in a downward direction, but prevents them from moving upwardly. A cutter 100 is provided to cut the lasso 91 loose from the catheter. Cutter 100 is actuated by pulling in a proximal direction on stylet 62. The back of cutter 100 is contoured to slide over a projection 102 that causes the cutter to engage lasso 91 and force it against a backing member 103 so that the sharpened tip of cutter 100 will sever the lasso 91. After lasso 91 has been severed, the anchor member 94 remains with the lasso and is disconnected from the catheter body 105 by rotation of the catheter body to disconnect a threaded connection as shown. A retaining ring 104 holds the cutter and backing member in place centrally within the catheter body 105.

An alternative embodiment for attaching the appendage 16/17 uses an inverting catheter described above and the tying catheter 88 with a lasso member 90 previously described via a thoracostomy. The probe system is inserted through an opening made in the intercostal space of the rib cage and advanced through the pericardium where it contacts the appendage 16/17. The inverting catheter is attached to the distal end of the appendage 16/17 with techniques previously described and is pulled so as to stretch the appendage structure 16/17 away from the main body of the atrium. Then, the lasso member 90 is wrapped over the stretched appendage 16/17 as far toward the main atrial body as possible. The lasso member 90 or 91 is subsequently tightened using techniques described above to isolate as much of the appendage 16/17 as possible. Subsequently, the appendage 16/17 may be cut and permanently removed by advancing another probe with a cutting surface to cut the neck of the appendage pouch leaving the lasso member 90 or 91 holding the rest of the appendage in place. Additionally, the lasso member 90 or another cauterizing probe may be used to fuse the appendage walls 16/17 together as will be described below for additional support after cutting off the appendage 16/17.

A further modified affixing embodiment is shown in FIGS. 23–24B. In this embodiment, a helical coil catheter 50 as shown in FIG. 7 is used in conjunction with a lasso applying catheter 88 which applies a lasso member 90 around the inverted appendage 16 or 17. The hollow lumen of the helical distal end 58 of catheter 50 is used to infuse a chemical fixing agent such as a cyanoacrylate 89, which after curing, affixes the inverted appendage 16 or 17 in the position shown in FIG. 25. While a cyanoacrylate is the preferred adhesive used in conjunction with this embodiment of the invention, other materials, for example other acrylate based adhesives such as polymethyl methacrylate or other biocompatible materials can be substituted.

The catheter infusion lumen may have a Teflon® polytetrafluoroethylene (PTFE) or similar inert material surface inside to reduce the extent of adhesive curing in the lumen prior to injecting the adhesive into the desired region. Also, more than one lumen may be contained within the catheter body to connect the helical coil hollow distal section to the injection site at the handle. As seen in FIG. 25, separate lumens 48 and 49 may be used to inject adhesive 89 and a contrast material to enable the injection of either contrast material or adhesive into the desired region without needing to displace the dead volume of another material from the lumen. Thus, one is able to quickly inject contrast at any point during the procedure to ensure the catheter has not moved while injecting the chemical adhesive. Also, an additional lumen may be required to inject simultaneously a catalyst and an adhesive to enhance the curing of the adhesive in the desired region. In FIG. 25 lumens 48 and 49 both discharge into a enlarged area 47 in distal tip member 54A, which in the case of two part curable materials can be used to provide for mixing of the two components. The desired ratio of catalyst to adhesive for proper curing may be achieved by designing the ratio of the respective lumen diameters to match this ratio and controlling the respective infusion stylets to move simultaneously.

The infusion lumens are preferably formed by extruding a PTFE tube and braiding a layer thereover of metal or polymeric plastic material. Thereafter and outer layer, preferably of a polyamide or polyester polymer is applied by dipping or extrusion.

After the adhesive material has solidified, the lasso member 90 may be expanded free from the appendage walls 16/17 preferably by releasing backward pressure on the retracting stylet 62 thus allowing the lasso member to loosen. Alternatively, an extending handle assembly may be actuated to open the lasso member 90 thereby loosening it. For this application, lasso member 90 should not have a latching mechanism, as shown in a prior embodiment, 91, so it may be readily released upon demand. After loosening the lasso member 90, the catheters may be removed from the vasculature.

Referring to FIG. 26, a releasable lasso member 142 may be manufactured from electrical conductors such as platinum/iridium, gold, stainless steel, or other metallic coils or rings and may be attached through electrically conductive wires 141 traversing the catheter lumen 140 to a radiofrequency generator, such as the EPT-1000, which transmits current at 500 kHz to the lasso member 142 to resistively heat the appendage walls 16/17. This electrically isolates the appendage 16/17 to ensure no arhythmogenic fibrillation, tachycardia, and/or flutter originates from the trabeculated appendage. In addition, heating the appendage walls can thermally fuse the adjacent appendage walls together producing a bond to hold the appendage 16/17 in the inverted position. Alternatively, heating changes the structure of the tissue through desiccation to change the shape of the appendage 16/17 even if a thermal bond of adjacent walls is not achieved because the required bonding temperatures are not reached. These changes in structure will help maintain the appendage 16/17 in the altered position. Of course, temperature sensors placed in the lasso member 142 may be used to regulate the heating to controllably ablate the appendage walls and/or thermally fuse adjacent walls together. Devices usable for this purpose are shown in greater in commonly owned copending application Ser. No. 08/439,824 filed May 12, 1995, the disclosure of which is incorporated by reference herein.

The composite loop structure 78 previously described may also be formed of an electrically conductive material and used to thermally heat and/or fuse the appendage 16/17 as described above.

Another method for affixing the appendage walls in an inverted or alternative position involves to insertion of an attachment member into or over the appendage 16/17. This technique may be implemented when attaching the appendage in an inverted position or pulling adjacent appendage walls together to produce a sack with the appendage pouch separated from the atrium.

FIG. 27A illustrates a mesh 95 constructed from a memory elastic material with temperature responsive transitional properties and/or superelastic properties, for example nickel titanium. Alteratively, a plastic material with elastic properties or stainless steel 17/7 may be utilized. The mesh 95 may be expanded over the inverted appendage with the catheter 130 shown in FIGS. 27B and 27C. Alternatively, the mesh 95 may be introduced into the pericardial space with a catheter of the type shown in FIGS. 29 and 30. In this case, a sharpened hollow needle 66 is introduced through the appendage wall 16/17 into the pericardial space. Then, a separately actuated stylet 62 is manually or automatically extended to insert the mesh attachment member 95 through the end of the hollow needle where it expands to its resting shape at body temperature to maintain the appendage 16/17 in said shape.

Referring now to FIGS. 27A–C more particularly, there is seen an attaching catheter 50 which is sized to fit within an inner lumen 128 located in mesh introducing catheter. The attaching catheter 50 and the mesh introducing catheter 130 may be simultaneously introduced into the atrium. Alternatively, the attaching catheter 50 can be introduced into the atrium and attached to an appendage wall 16–17. The introducer catheter 130 can then be guided over the appendage attaching catheter 50. The mesh 95 is seen in its resting configuration in FIG. 27B.

Mesh 95 is supported within an introducer sheath 132 and on a base plate or cylinder 134 which is provided with an annular opening 136 to allow catheter 50 to fit therethrough. Preferably, a retaining ring 138 is provided to hold the wires 140 which may be, for example, in the form of a suture or wire.

In use, catheter 130 is introduced over catheter 50 in the appendage 16/17. The introducer sheath 132 and the retaining ring 138 and thus the pull wires 140 are retracted proximally forcing the distal end of the mesh to expand radially. The expanding mesh 95 is then advanced over the inverted appendage 16/17. Subsequently, the wires 140 are released from retaining ring 138 allowing the mesh 95 to close over the atrial appendage 16/17. The wires 140 are then retracted into sheath 132 and the assembly is then removed from the vasculature.

Two alternative handle designs for the various catheters referred to above are shown in FIGS. 33A and 33B. In FIG. 33A, a fixed introduction tube assembly 150 has an internal lumen 152 in which expandable anchors and/or a stylet may be inserted. In FIG. 33B, the introduction tube assembly 170 is axially moveable. In one embodiment, separate attaching and grasping catheters are used as a system. In an alternative embodiment, a single catheter of the type shown in FIGS. 29 and 30 with an integrated grasping mechanism, such as a helical coil, may be used.

In FIG. 33A there is seen a typical catheter steering and manipulating mechanism. Catheter body 52 having a distal tip portion 54 extends distally from a handle portion 64 which contains a steering handle 63 to which steering wires 61 are attached to effect bending of steering mechanism 57 remotely from handle 63. Conductive wires 65 may be included in the event that it is desired that, for example, a mapping electrode be positioned on distal tip 54 to detect electrical activity within the heart.

The embodiment of FIG. 33A includes an expandable anchor introduction and/or push rod port 67 and a separate infusion port 68 through which liquids can be introduced when needed in accordance with the above-described procedures. A porous membrane or slotted hollow tube 71 can be provided to allow flow of liquids from port 68 into the lumen of introducer port 67. In the embodiment shown in FIG. 33B, a push rod 69 is included for the purpose of advancing expandable anchors or other components introduced into the atrium in accordance with the invention. Advancing of rod 69 distally will advance the materials contained in the introduction lumen 67 in a distal direction into the atrium. In this latter embodiment the entire infusion assembly 150 is axially movable so that the same can be advanced manually in order to effect tissue penetration when required in accordance with the foregoing descriptions.

FIG. 28 shows a helical winding used as an attachment member 96 for holding the appendage 16/17 in place. The catheter shown in FIGS. 29 and 30, and the handle assemblies shown in FIG. 33A or 33B may be used to introduce the helical winding 96. The helical winding 96 is preferably made from a memory elastic material as described above. The helical winding 96 is introduced in an extended shape which may easily be pushed into the appendage walls 16/17 and after the helical winding 96 extends beyond the hollow needle 66 via extension of the stylet 62, the helical winding 96 expands into its resting shape holding the appendage 16/17. Alternatively, the helical winding 96 may be made from a stiffer material such as stainless steel 17/7 and screwed into the tissue.

FIG. 29 is a sectional view of a catheter which may insert the metallic mesh 95, the helical winding of FIG. 28, or other material with an elastic memory into or through the inverted appendage to maintain the appendage in the inverted position. FIG. 29 shows a catheter 110 having a hollow needle distal tip portion 66 that contains an attaching expandable anchor 116. The hollow needle is reciprocally fitted in a distal tip member 114 which has a central opening sized to allow reciprocation therein of the hollow needle 66. Distal tip 114 is secured by conventional means to a catheter body 112 within which is provided a steering mechanism 57 as described above. Also, fitted reciprocally within hollow needle 66 is a pushing stylet 118 which is utilized to expel expandable anchor 116 after the proper location has been reached through use of the sharp and hollow needle 66. After the tip has been placed in the desired position, the expandable anchor is expelled from the needle by extending stylet 118 and subsequently retracting the hollow needle 66 and the pushing stylet 118 within the rounded distal tip member 114.

Methods & Devices for Affixing Adjacent Appendage Walls

FIGS 31A–31C show a mechanism which creates a purse-string-like constriction around the interior surface of an appendage 16 or 17 (or other body cavity). This arrangement enables pulling of adjacent walls together, thus forming a tightened sack in which the pouch of the appendage is separated from the remainder of the atrium. Expandable anchors 116 of the type shown in FIG. 31C or expandable anchors 120 shown in FIG. 32 may be introduced through the appendage wall 16/17 by means of a catheter similar to the one shown in FIG. 29. In such case multiple expandable anchors 116 or 120 are placed within the hollow needle 66 and are interconnected with a suture, wire, or similar material 126. The suture 126 may be fed through a loop 117 in the expandable anchor 116 to permit remote tightening of the appendage walls after all expandable anchors 116 have been placed or may be secured to each of the expandable anchors 116 to tighten the walls 16/17 as the expandable anchors are being placed. Ultimately, the appendage walls 16/17 will be pulled together by the suture material 126 in the form shown in FIG. 31B. To separate the pouch from the atrium, a filler material such as silicone or collagen may be inserted into the appendage pouch to fill the pouch and minimize or eliminate blood flow into or out of the pouch. Also, a memory elastic mesh 95 may be inserted into the pouch or over the sack entrance for additional support and to prevent thrombus movement from the pouch into the atrium. Also, in this embodiment, the blood inside the pouch will clot, forming a naturally occurring support structure for the separated appendage 16/17.

When the form of expandable anchors 120 of FIGS. 32A and 32B are used, suture material 126 may be continuously fed through a central lumen 124 of pushing stylet 124 as shown.

Referring to FIGS. 34 and 35, there is seen a procedure for reducing the volume of an appendage 16 or 17 by means of a thoracostomy. In this case, the pericardium is penetrated by means of an incision passing through the rib cage. The incision is entered by a grasping catheter, for example catheter 70 as already described hereinabove. Thereafter, a lasso 90 or 91 can be utilized to tie off the neck of the appendage 16 or 17 as seen in FIG. 34 utilizing a catheter 170 shown in FIG. 35. The appendage can also be fixed in a repositioned location with reduced volume by sutures, staples, memory wire, biocompatible adhesives, or by tissue ablation as described above.

As seen in FIG. 35, catheter 170 includes a flexible catheter body 172 having a distal tip portion 174. A lumen or tubular guide 176 is provided for allowing the lasso 90 to be freely axially movable so that the lasso 90 can be expanded or contracted. Also as seen in FIG. 35, the lasso 90 may have an enlarged end 8 for the purpose of anchoring the same in catheter distal tip 174 as shown. Utilizing this arrangement, the appendage 16 or 17 can be permanently fixed in the altered position utilizing staples, sutures, chemical bonding agents or by means of ablation. Alternatively, also a locking or ratcheting loop 91 of the type described above can be permanently put in place to tie off the neck of the appendage 16 or 17.

It should be appreciated that the repositioning and affixing methods and devices described above may apply to aneurysms, or any other body cavities that naturally or pathologically exist.

What is claimed is:

1. An apparatus for electrically isolating a portion of an atria, the atria including atrial walls having outer surfaces, the apparatus comprising:

a handle; and an energy transmission structure, associated with the handle, including at least two energy transmission surfaces;

the energy transmission structure being configured and dimensioned such that it is movable between a first orientation where a distance between the at least two energy transmission surfaces is sufficient to accommodate at least two atrial walls that substantially oppose one another and a second orientation where the distance between the at least two energy transmission surfaces will cause the at least two atrial walls to be in contact with one another.

2. An apparatus as claimed in claim 1, wherein the energy transmission structure comprises a releasable lasso.

3. An apparatus as claimed in claim 1, wherein the mission surfaces comprise ablation surfaces.

4. An apparatus as claimed in claim 1, wherein the energy transmission surfaces comprise electrically conductive material.

5. An apparatus as claimed in claim 1, further comprising:

a connector for connecting the energy transmission surfaces to an energy source.

6. An apparatus as claimed in claim 1, wherein the energy transmission structure is configured and dimensioned such that the distance between the at least two energy transmission surfaces is sufficient to accommodate at least two atrial appendage walls that substantially oppose one another when the energy transmission structure is in the first orientation and the distance between the at least two energy transmission surfaces will cause the at least two atrial appendage walls to be in contact with one another when the energy transmission structure is in the second orientation.

7. An apparatus as claimed in claim 1, wherein the at least two energy transmission surfaces are connected to one another, thereby defining a continuous energy transmission surface.

8. An apparatus as claimed in claim 1, wherein the energy transmission structure is configured and dimensioned such that the distance between the at least two energy transmission surfaces is sufficient to accommodate at least two left atrial walls that substantially oppose one another when the energy transmission structure is in the first orientation and the distance between the at least two energy transmission surfaces will cause the at least two left atrial walls to be in contact with one another when the energy transmission structure is in the second orientation.

* * * * *